(12) United States Patent
Tran-Thi et al.

(10) Patent No.: US 8,647,885 B2
(45) Date of Patent: Feb. 11, 2014

(54) PROCESS FOR DETECTING GASEOUS HALOGENATED COMPOUNDS

(75) Inventors: Thu-Hoa Tran-Thi, St. Fargeau-Ponthierry (FR); Philippe Banet, Perpignan (FR); Loic Legagneux, Martinique (FR)

(73) Assignees: Commissariat a l'Energie Atomique, Paris (FR); Centre National de la Recherche Scientifique (CNRS), Paris (FR)

( * ) Notice: Subject to any disclaimer, the term of this patent is extended or adjusted under 35 U.S.C. 154(b) by 469 days.

(21) Appl. No.: 12/598,327

(22) PCT Filed: May 2, 2008

(86) PCT No.: PCT/FR2008/050783
§ 371 (c)(1),
(2), (4) Date: Oct. 30, 2009

(87) PCT Pub. No.: WO2008/148987
PCT Pub. Date: Dec. 11, 2008

(65) Prior Publication Data
US 2010/0136704 A1 Jun. 3, 2010

(30) Foreign Application Priority Data
May 4, 2007 (FR) ..................................... 07 03238

(51) Int. Cl.
*G01N 21/03* (2006.01)
(52) U.S. Cl.
USPC ............. 436/165; 436/43; 436/124; 436/164; 436/172; 422/50; 422/83
(58) Field of Classification Search
None
See application file for complete search history.

(56) References Cited

U.S. PATENT DOCUMENTS 4,529,707 A 7/1985 Cowles et al.
4,801,380 A * 1/1989 Parker et al. ............. 210/500.21

(Continued)

FOREIGN PATENT DOCUMENTS

FR 2 856 150 12/2004
FR 2856150 12/2004

(Continued)

OTHER PUBLICATIONS

Mitra, Smarajit. "A polymeric triarylmethane dye as a sensitizer for photoconductivity". 1986. Journal of Polymer Science. vol. 74. pp. 165-169.*

(Continued)

*Primary Examiner* — Robert Xu
(74) *Attorney, Agent, or Firm* — Frost Brown Todd LLC

(57) ABSTRACT

Process for detecting a gaseous compound of $BX_3$, $HX$ or $X_2$ type within a gas using a composition containing a probe molecule, characterized in that the probe molecule is a molecule for which the reaction with one or more compounds of $BX_3$, $HX$ or $X_2$ type leads to a variation of at least one of its physicochemical properties, this variation being measurable via a suitable analysis technique, and in that the following steps are carried out in this order: (a) measurement of said physicochemical property of the probe molecule, such as a spectral property, (b) bringing the gas into contact with the composition containing the probe molecule from step (a), (c) repeat measurement of said physicochemical property, (d) correlation of the variation of said spectral property between steps (a) and (c) in the presence of said gaseous compound of $BX_3$, $HX$ or $X_2$ type, the measurement of the physicochemical property from step (a) possibly being a prior step, process for trapping gaseous compounds of $BX_3$, $HX$ or $X_2$ type contained in a gas, material capable of reacting with at least one compound of $BX_3$, $HX$ or $X_2$ type in gaseous form and sensor for compounds of $BX_3$, $HX$ or $X_2$ type.

10 Claims, 15 Drawing Sheets

(56) References Cited

U.S. PATENT DOCUMENTS

| | | | |
|---|---|---|---|
| 4,820,316 | A | 4/1989 | Mizuno et al. |
| 6,773,925 | B2 | 8/2004 | Ibaraki et al. |
| 7,892,851 | B2 * | 2/2011 | Tran-Thi et al. ............... 436/172 |
| 2001/0012635 | A1 | 8/2001 | Ibaraki et al. |
| 2007/0214867 | A1 | 9/2007 | Tran-Thi et al. |

FOREIGN PATENT DOCUMENTS

| | | | |
|---|---|---|---|
| FR | 2 869 036 | | 10/2005 |
| JP | 57 094652 | | 6/1982 |
| JP | 57094652 | | 6/1982 |
| JP | 60 140 209 | | 9/1985 |
| JP | 01082776 | | 3/1989 |
| JP | 4330298 | | 11/1992 |
| JP | 9 249815 | | 9/1997 |
| JP | 09249815 | * | 9/1997 |
| JP | 63047640 | | 2/1998 |
| RU | 2 017 689 | | 8/1994 |
| RU | 2017689 | | 8/1994 |
| SU | 967945 | | 10/1982 |
| WO | WO 2008/148987 | | 12/2008 |

OTHER PUBLICATIONS

International Search Report dated Jun. 23, 2009 for Application No. PCT/FR2008/050783.

Written Opinion (translation) dated Dec. 7, 2009 for Application No. PCT/FR2008/050783.

Bourgeois, A. et al., "Determination of pore size distribution in thin organized mesoporous silica films by spectroscopic ellipsometry in the visible and infrared range," Thin Solid Films (2004) pp. 447-448 and 46-50.

Kikuchi, Y. et al., "Properties of membranes from polyelectrolyte complexes consisting of methyl chitosan, [2-(diethylamino)ethyl]dextran, and poly(potassium vinyl sulfate),"Makromol. Chem., vol. 188 (1987) pp. 2631-2642.

Office Action dated Nov. 1, 2011 for Application No. JP2010-504814.

Office Action dated Nov. 2, 2011 for Application No. JP2010-504814 (translation).

* cited by examiner

NaI    KI    KBr    NaCl    $(C_{15}H_{33})(Me)_3N^+, Br^-$
*ms1*   *ms2*  *ms3*   *ms4*    *ms 5*

$(Bu)_4N^+, I^-$     $^-Br, (Me)_3N^+-(C_{10}H_{22})-N^+(Me)_3, Br^-$
*ms6*                *ms7*

$HO(CH2)(Me)_3N^+, I^-$
*ms8*

*ms9* : chitosan glycol methyl trimethylammonium iodide

*ms11* : M = Mg
*ms12* : M = Si(CH$_3$)$_2$
*ms13* : M = Cu

*ms10*

*ms14*

*ms15*

PROCESS FOR DETECTING GASEOUS HALOGENATED COMPOUNDS

PRIOR ART

The present invention relates to the field of metrology of halogenated derivatives of boron as well as corresponding halogens and halogenated acids, for example in contaminated environments, as well as the pollution control of said environments.

Halogenated derivatives of boron currently play a significant role in the semi-conductors industry. In fact, due to its electronic configuration, boron is considered to be a particularly useful p-type dopant. Also, in order to ensure specific properties to silicon substrates, the electronics industry is a heavy consumer of compounds such as $BF_3$ or the $BCl_3$. These gaseous compounds remain difficult to handle and their toxicity is particularly severe inasmuch as they can cause delayed damage, in particular in the case of inhalation, and lead to fatal pulmonary oedema. The decomposition of boron halides often leads to the formation of the corresponding hydrogen halides.

The properties of halogens and the corresponding acids and their relative stability have been exploited for longer than boron derivatives. Various industries currently use these compounds in their day-to-day operations.

Chlorine is used in particular by the chemical industry for the preparation of polymers such as polyvinyl chloride (PVC) or also for the preparation of solvents, herbicides or coolants. Although it use is now decreasing in the production of pastes and paper, gaseous chlorine is still a substance widely used for whitening. It is also used in metallurgy, in particular for the production of titanium oxide, and in plasma form in electronics for the production of semiconductors. Its recognized biological toxicity is exploited for purification of aqueous environments. Fluorine is essentially used in particular in the nuclear industry for the synthesis of uranium hexafluoride by fluorination of uranium oxide. Bromine, which is less used, is useful in particular in the production of chemical products such as pesticides or herbicides.

Acid derivatives of halogen are also used in different fields of activity. The production of chlorinated compounds and chlorinated chemical products such as methyl chloride or benzyl chlorides, metallic chlorides (such as aluminium or silicon chlorides) require the use of HCl. Hydrogen chloride is also used in hot-galvanizing or mineral-separation processes; in electronics it is exploited both in the production of semiconductors and as a moisture trap. Hydrogen fluoride has overall the same applications, in addition to its use in uranium processing methods. Apart from the direct effects of their acidity on materials and living organisms, both externally (cutaneous and ocular) and internally (in particular on the lungs), there can be more specific effects. This is the case of hydrofluoric acid in particular, which like fluorine, can cause lethal problems associated with hypocalcaemia in biological organisms.

Moreover, some of these gases are particularly flammable compounds, and the products of their combustion are also often harmful.

Considering the high toxicity of all compounds mentioned, it is important to provide users with maximum safety while handling such products. The high reactivity of these compounds demands particularly effective and secure storage conditions. However, whatever precautions are used for handling highly reactive gaseous compounds, it is essential that effective detection measures are in place as a precaution against any escape in the system used.

For most of these compounds, the concentrations currently permitted in the work environment are generally comprised between 0.1 and 10 ppm.

The processes for detecting halogenated compounds, particularly halogenated boron complexes, known from the prior art are in most cases based on colorimetric detection based on coloured reagents in liquid solution or impregnated reagents on solid supports of the alumina, silica gel, activated carbon, $TiO_2$ bentonite, clay, carbonate or also zeolite type.

A process for detecting $BCl_3$ using curcumin was developed within the context of the purification of metallic silicon for the semiconductor industry. It involves several stages, including processing the chlorosilane sample to be analyzed with mannitol in order to form a non-volatile compound with boron. The solution is then hydrolyzed then fluorinated before being extracted. The residual boron compound is then treated with curcumin in a non-aqueous acid medium and leads, by reaction of the curcumin with boron cations, to the formation of a red complex (rosocyanin) absorbent at 540 nm, which allows a quantitative analysis of the boron complex with a sensitivity of 50 ppb.

The boron-based impurities in the chlorosilane can be also extracted by treatment with quinalizarine in sulphuric acid. This intense blue-violet solution which turns red on adding water reverts to its initial colour in the presence of boron compounds. Colorimetric analysis at 630 nm allows quantitative measurement of boron compounds with a sensitivity of 5 ppb, according to U.S. Pat. No. 4,529,707.

A spectrophotometry process based on monitoring the absorbance of a $BF_3$:EtOH complex at 275 nm was developed in order to study the formation in solution of stable complexes of $BF_3$ and an alcohol (MeOH, EtOH) or ethers, $(Et)_2O$ or p-dioxane.

Among the reagents used on a solid support there can be mentioned curcumin, also used in liquid phase, which makes it possible to detect $BCl_3$ but also $SiH_2Cl_2$, HF, $F_2$, HBr, $Cl_2$ or bromocresol green which makes it possible to detect $SiHiCl_2$, HF, $Cl_2$, $BCl_3$, $SiHCl_3$ and $BF_3$. Thus in U.S. Pat. No. 6,773,925, these two compounds, deposited on activated alumina, are used in colorimetric detectors having a sensitivity comprised between 0.5 and 5 ppm.

Carminic acid can also be used for colorimetric detection of $BCl_3$ in the presence of hydrochloric acid and sulphuric acid, as described in Japanese Patent Application No. 60-140209. U.S. Pat. No. 4,820,316, although it does not exploit the colorimetric variations of this compound, proposes to measure the variations in mass of a material containing in particular carminic acid or dianthramide as well as hydrochloric acid and sulphuric acid in order to detect $BCl_3$.

The reaction between β-diketones grafted in a porous matrix and $BF_3$, leading to the formation of highly absorbent and fluorescent benzoylmethanatoboron difluoride, was described in French Patent Application No. 2 869 036 for the assay of gaseous $BF_3$.

For the detection of other halogenated compounds, reagent tubes exist impregnated with colorant which changes colour in the presence of a halogenated derivatives. For example for chlorine and/or bromine, it is ortho-toluidine or ortho-tolidine which take on a brown-orange colour. For HCl, bromophenol blue becomes yellow.

Detection processes based on electrochemical measures are also known.

From the work carried out to date it appears that few processes can be used in a direct, rapid and effective fashion in order to detect and/or collect halogenated boron compounds, corresponding acids as well as halogens.

Moreover, none of these processes allows these different compounds to be detected simultaneously.

Considering the reactivity and toxicity of these compounds, it is essential to offer users varied, safe and rapid means for detecting relatively low concentrations in the atmosphere, particularly in the work environment. Moreover, in particular in the electronics field where different compounds can be present simultaneously, it can be useful to monitor the presence of each one. Moreover, the ability to assay these compounds would be advantageous.

The process of detection, quantification and trapping proposed by the present patent application resolves this shortcoming in a safe and effective fashion.

DESCRIPTION

A particular subject of the present invention is a process for detecting halogenated boron derivatives, halogens and corresponding acids. The process relates in particular to detecting gaseous compounds of formulae $BX_3$, HX and $X_2$, in which X represents a halogen, using probe molecules.

This process also makes it possible to quantify the amount of compound detected.

A particular subject of the invention is therefore a process for detecting a gaseous compound of $BX_3$, HX or $X_2$ type within a gas using a composition containing a probe molecule, characterized in that the probe molecule is a molecule for which the reaction with one or more compounds of $BX_3$, HX or $X_2$ type leads to a variation of at least one of its physico-chemical properties, this variation being measurable via a suitable analysis technique, and in that the following steps are carried out in this order:
  (a) measurement of said physico-chemical property of the probe molecule, such as a spectral property,
  (b) bringing the gas into contact with the composition containing the probe molecule from step (a),
  (c) repeat measurement of said physico-chemical property,
  (d) correlation of the variation of said spectral property between steps (a) and (c) in the presence of said gaseous compound of $BX_3$, HX or $X_2$ type.

The measurement of the physico-chemical property of step (a) is possibly a prior step, carried out once for all, such that the process of the invention, routinely no longer comprises step (a).

The gaseous compound of $BX_3$, HX or $X_2$ type is for example HBr, HF, $F_2$, $Br_2$ and in particular, HCl, $Cl_2$, $BCl_3$, or $BF_3$ It can be present in a gas such as those encountered in particular in the production or research facilities of various industries such as those mentioned previously, and particularly in the semiconductors industry.

Bringing the gaseous mixture and the composition into contact can be carried out directly, typically in the presence of a stream of the gaseous mixture, or also under reduced pressure, or after dissolution of the gaseous compound by bubbling through a liquid solvent, bringing the components of the gaseous mixture and the composition into contact being carried out in the liquid medium constituted by the solvent and the dissolved gas mixture. In a preferred fashion, the bringing into contact is carried out directly without dissolution in a liquid solvent.

The physico-chemical property in question can be in particular a spectral property, such as absorbance, which can be measured by reflection or transmission, fluorescence, luminescence, or an electrical property such as conductivity, dielectric constant, or other properties such as resistivity or mass.

The measurement can be a simple detection.

The physico-chemical property variation is linked to the reaction of the probe molecule with one or more compounds of $BX_3$, HX or $X_2$ type, it resides in the existing structural differences between the probe molecule and the reaction product of the probe molecule with the compound to be detected.

By "composition", is meant a compound or mixture of compounds, which is advantageously in solid form and will typically comprise a matrix and in particular a porous matrix.

The composition can in particular be constituted by the probe molecule only, in particular when the latter is a polymer.

It can also contain surfactants, the role of which is either to increase the solubility of the probe molecules in the composition, or to structure the porous matrices by forming cavities having a particular size and shape.

By "probe molecule" is meant any molecule for which the reaction with one or more compounds of $BX_3$, HX or $X_2$ type leads to a variation of at least one of its physico-chemical properties, detectable via a suitable analysis technique. By taking into account the nature of the physico-chemical property in question, a person skilled in the art can easily determine the appropriate detection technique. Thus, a modification of the spectral properties can be detectable by spectrophotometry. For this reason, it is possible to speak of modification of the spectrophotometric properties. Several modifications of detectable physico-chemical properties can take place during implementation of the process. It is possible to use one or more of these modifications. The variation of the physico-chemical properties of a probe molecule can be detected from the composition which may contain it, when it is a question of measuring the physico-chemical properties for a probe molecule, before or after reaction with one of the gases, it must be understood of course that the measurement can be carried out on a composition containing the probe molecule, thus it is possible by extension to speak of "measuring a property of the composition" equally well as "measuring a property of the probe molecule". In other words, the measurement can be carried out on the probe molecule or on the composition in which it is contained. The structure of the probe molecule can be modified at the end of the reaction. Thus it is possible that the probe molecule as such has no notable property at the start, but that its reaction product has a notable property, for example a spectral property. The variation observed at the end the reaction makes it possible to detect the presence of the sought gaseous compound.

Thus, the probe molecule is characterized by properties, for example spectral properties, before and/or after reaction with a $BX_3$, HX or $X_2$ type compound. The absorption and/or fluorescence spectra, for which the variation is measurable by an appropriate spectrophotometric process known to a person skilled in the art, are particularly concerned. For example, the probe molecule can be a chromophore for which the absorption and/or fluorescence spectra are modified by reaction with a compound of $BX_3$, HX and/or $X_2$ type. By "modification of the absorption and/or fluorescence spectra", is meant in particular an effect such as a loss or gain in the intensity of absorption or fluorescence at a given wavelength, a shift in the wavelength of the absorption and/or fluorescence maxima, or also the appearance of new bands. The measured property can also correspond to the interaction with Love type waves, linked to the dielectric constants, but also to a mass or to viscoelasticity.

The probe molecules which can be used according to the invention are in particular alkali metal halides, quaternary ammonium halides, coumarin and its derivatives, porphyrazine and its derivatives, fluorescein and its derivatives and triarylmethanes. Rhodamines, cresyl violet, derivatives of phenoxazine and oxazones can also be mentioned. More particularly, alkali metal halides (NaI, KI, KBr, NaCl), quaternary ammonium halides (chitosan methylglycol trimethylammonium iodide, decamethonium dibromide and 3-hydroxypropyltrimethylammonium iodide, coumarins 522, 500, 120, 102, 47, magnesium, silicon, dilithium and disodium phthalocyanines, fluorescein and crystal violet.

The probe molecules can be used to detect all compounds of $BX_3$, HX and $X_2$ type or only some of them.

They can react differently depending on the compound of $BX_3$, HX and $X_2$ type and thus give qualitative information on the nature of the detected compound or its absence.

Preferred alkali metal halides are KI, KBr, KCl, NaI, NaBr and NaCl. It is remarkable that an alkali halide can generally be used for detecting a compound comprising the same halide. For such probe molecules the spectrophotometric property measured is in particular absorbance. The observed wavelength corresponds to that of the halogenated derivative formed, such as $I_3^-$ $Br_3^-$ or $Cl_3^-$, or an inter-halogenated derivative, such as $BrCl_2^-$, $Br_2Cl^-$, which has a specific absorption spectrum. Thus for example, during the exposure of KBr to $Br_2$, the variation in the absorbance is linked to the formation of $Br3^-$ which has a specific absorption spectrum. These probe molecules are characteristic of the compounds of $BX_3$ and $X_2$ type. They do not react significantly with compounds of HX type.

Among the quaternary ammonium halides, it is advantageous to use those of formula (I):

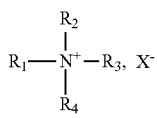

in which:

$R_1$, $R_2$, $R_3$ correspond independently to an H or a carbon-containing chain comprising from 1 to 22 carbon atoms, $R_4$ is chosen from the carbon-containing chains and the polysaccharides, X is a halogen preferably I, Br or Cl.

A carbon-containing chain can optionally be mono- or polysubstituted, linear, branched or cyclic, bridging or not, saturated or unsaturated, $C_1$-$C_{22}$, preferably $C_1$-$C_{10}$, the substituent(s) being able to contain one or more heteroatoms such as N, O, F, Cl, P, Si or S. Among such carbon-containing chains the preferred alkyl radicals are methyl, ethyl, propyl, isopropyl, butyl, isobutyl, tert-butyl and pentyl radicals. Among the unsaturated alkyl radicals, vinyls, allyls, isopropenyls, butenyls, isobutenyls, tert-butenyls, pentenyls and acetylenyls can be mentioned.

An aryl radical corresponds to a carbon-containing structure which is aromatic or heteroaromatic, mono- or polysubstituted, constituted by one or more aromatic or heteroaromatic rings each comprising 3 to 8 atoms, the heteroatom being able to be N, O, P, F, Cl, Si or S.

Preferably $R_1$, $R_2$, $R_3$ are aliphatic groups chosen independently from H, $CH_3$, $C_2H_5$, $C_3H_7$, $C_4H_9$, $CH_2(C_6H_5)$, $CH_2(C_6H_{11})$, $C_6H_{11}$.

Preferably, $R_4$ is a $C_1$-$C_{22}$ carbon-containing chain and more particularly a $C_1$-$C_{22}$ alkyl group in particular of formula $-(CH_2)_n-CH_3$ with n=1 to 21, and typically a $C_{11}$-$C_{21}$ group, advantageously comprising at least one ammonium, an aryl, a cyclohexyl, a cetyl, or also a polysaccharide chosen in particular from cellulose, chitosan or their derivatives.

A polysaccharide is a polymeric structure composed of a large number of monosaccharide units joined by glycosidic bonds, the units are able to be independently substituted, the substituent(s) are able to contain one or more heteroatoms such as N, O, F, Cl, P, Si or S as well as alkyl or aryl radicals. As the mass of the polymer affects its viscosity, the use of a probe molecule of polysaccharide type is easier if the average degree of polymerization, or average number of monomers in the polymer (m), is comprised between 2 and 100,000, particularly between 10 and 20,000, more particularly between 20 and 1,000.

In the case where $R_4$ is a polysaccharide, it typically contains from 100 to 500 monomers. The monomeric unit bearing the ammonium is preferably of formula (I'):

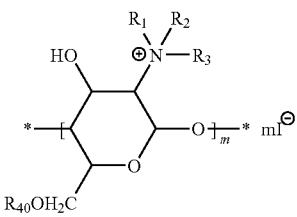

in which $R_{40}$ corresponds to a hydrogen or to a $C_1$-$C_{12}$ generally carbon-containing chain, advantageously comprising an ether-oxide function; this is particularly a $CH_3OC_2H_4$- group. X corresponds to a halogen, and preferably to a Cl, Br or I, as defined previously. It is preferable that $R_1$ $R_2$ and $R_3$ correspond independently to H's or $C_1$-$C_4$ alkyl groups, preferably $C_1$.

When $R_4$ is a polysaccharide constituted by monomeric units shown above, it is of course possible that the nitrogen number present in the form of ammonium is variable. It can vary theoretically from 1 to m, it is recommended that the quantity of monomeric unit comprising an ammonium within the polymer is either comprised between 40 and 90% of the total quantity of monomeric unit, typically it will be close to 70%.

Moreover, it is advantageous that the quaternary ammonium has surfactant properties, it is also advantageous that it is in the form of a cationic polymer.

Advantageously the quaternary ammonium halide probe molecule is cetyltrimethylammonium bromide (CTAB) or chitosan methylglycol trimethylammonium iodide (Kikuchi, Y., et al. Makromol. Chem. 188 & 108. 2631 & 6776c, (1987)), or tetrabutylammonium iodide or bromide.

For such probe molecules, the measured spectrophotometric property is preferably absorbance and the wavelength observed will correspond preferably to that of the product formed depending on the starting reagents. These probe molecules are characteristic of the compounds of $BX_3$ and $X_2$ type, they do not react significantly with compounds of HX type.

The probe molecules to which the invention relates also correspond to coumarin derivatives, in particular the derivatives for which the carbon in position 7 bears a nitrogen, preferably non-charged and of sp3 type and more particularly to the compounds of formula (II):

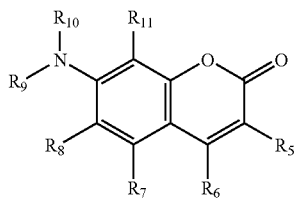

in which, $R_5$ and $R_6$ are chosen independently from H, alkyl or aryl radicals, preferably from H, the $C_1$-$C_{15}$ alkyl radicals, ketoalkyls, esters, fluoroalkyls such as trifluoromethyl, benzimidazoles, benzothiazoles, $R_7$ and $R_8$ are chosen independently from H, the $C_1$-$C_{15}$ alkyl radicals, $R_9$, $R_{10}$ and $R_{11}$ are chosen independently from H, the $C_1$-$C_{15}$ alkyl radicals.

Typically the probe molecule is thus chosen from the following coumarin derivatives (denomination and CAS number reference): coumarin 120 (CAS: 26093-31-2), coumarin 2 (CAS: 26078-25-1), coumarin 466 (CAS: 20571-42-0), coumarin 47 (CAS: 99-44-1), coumarin 102 (CAS: 41267-76-9), coumarin 152A (CAS: 41934-47-8), coumarin 152 (CAS: 53518-14-2), coumarin 151 (CAS: 53518-13-3), coumarin 6H (CAS: 58336-35-9), coumarin 307 (CAS: 55804-66-5), coumarin 500 (CAS: 52840-38-7), coumarin 314 (CAS: 55804-66-5), coumarin 30 (CAS: 41044-12-6), coumarin 334 (CAS: 55804-67-6), coumarin 522 (CAS: 55318-19-7), coumarin 7 (CAS: 27425-55-4), coumarin 6 (CAS: 38215-35-0) and coumarin 153 (CAS: 53518-18-6), coumarin 445 (CAS: 28821-18-36), coumarin 460 (CAS: 91-44-1), coumarin 461 (CAS: 87-01-4), coumarin 503 (CAS: 55804-70-1), coumarin 510 (CAS: 87349-92-6), coumarin 519 (CAS: 55804-65-4), coumarin 521T (CAS: 1 14768-72-8), coumarin 522B (CAS: 53518-19-7), coumarin 523 (CAS: 55804-68-7), coumarin 525 (CAS: 87331-47-3), coumarin 540 (CAS: 38215-36-0), coumarin 545 (CAS: 85642-11-1).

The spectral properties of these compounds are based in particular on the existence of the conjugated ring system and the presence of a nitrogen-containing donor group. Many compounds corresponding to the formula (II) have already been synthesized and are commercially available, in particular in the laser colorants industry, moreover their spectral properties have already been determined.

For such probe molecules the measured spectrophotometric property can be absorbance or fluorescence. For absorbance measurements, the wavelength of interest will correspond to that of the absorption band having the lowest energy, generally situated between 320 and 440 nm. As exposure progresses, the intensity of this band reduces and a new band shifted towards blue appears. The fluorescence of these probe molecules is comprised between 400 and 580 nm. These probe molecules are characteristic of compounds of HX and $BX_3$ type, and do not react with compounds of $X_2$ type.

Porphyrazine and its derivatives and in particular tetrabenzotetraazaporphyrins can also be used as probe molecules according to the invention. These are particularly compounds of formula (III):

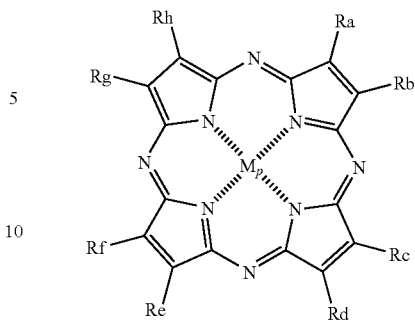

in which,

Ra to Rh independently correspond to H, sulphurated or phosphorated organic groups, such as acids, carbon-containing chains able to be optionally mono- or polysubstituted, linear, branched or cyclic, bridging or not, $C_1$-$C_{22}$ saturated or unsaturated, preferentially $C_1$-$C_{10}$, the substituent(s) being able to contain one or more heteroatoms such as N, O, F, Cl, P, Si or S. The preferred alkyl radicals are found from the carbon-containing chains, in particular methyl, ethyl, propyl, isopropyl, butyl, isobutyl, tert-butyl and pentyl radicals can be mentioned in this context. Among the unsaturated alkyl radicals, the vinyls, allyls, isopropenyls, butenyls, isobutenyls, tert-butenyls, pentenyls and acetylenyls can also be mentioned. This can also be an aryl radical corresponding to an aromatic or heteroaromatic, mono- or polysubstituted carbon-containing structure, constituted by one or more aromatic or heteroaromatic rings each comprising 3 to 8 atoms, the heteroatom can be N, O, P, F, Cl, Si or S. Inasmuch as Ra and Rb, Rc and Rd, Re and Rf or Rg and Rh can correspond to bridging groups linked to each other, the molecule can thus comprise a ring structure joined to one or more of the nitrogen rings at the core of the structure.

Preferably, Ra and Rb, Rc and Rd, Re and Rf or Rg and Rh together form an aromatic ring or correspond to a hydrogen; the molecule is advantageously tetrabenzoporphyrazine (phthalocyanine).

When Ra and Rb, Rc and Rd, Re and Rf or Rg and Rh form together an aromatic ring, the molecule can for example be synthesized by the condensation of four identical molecules of phthalonitriles.

Porphyrazine and its derivatives can optionally complex a cation or a group of cation M, therefore p corresponds to an index of 0 or 1 indicating the presence of this type of entity. This can be a metal, generally chosen from transition metals such as Fe, Co, Cu or Ni, for which the degree of oxidation is typically 2 or 3. Advantageously this metal will be Mg(II) or Cu(II). It is also possible that porphyrazine and its derivatives complex lighter elements such as Si (IV) or alkali metals. In this case the complexation of two atoms such as Li(I) or Na(I) is observed.

The spectrophotometric properties that it is recommended to observe for such molecules are fluorescence and absorbance. In absorption, a gradual disappearance of the transition of lower energy typically towards 690 nm and the correlated appearance of a new transition, for which the absorption maximum is shifted towards red can be observed simultaneously. This shift increases when $BX_3$ reacts successively with each of the 4 nitrogens of the aza bridges of the macrocycle. These spectral variations are accompanied by an isobestic point at approximately 560 nm. In fluorescence, by exciting the probe molecule at the isobestic point, the wavelength for which the number of photons absorbed will be constant, a fluorescence can be observed at approximately 560 nm, the spectrum of which is centred towards 700 nm, which undergoes a bathochromic shift when the film is exposed to $BF_3$. It is also possible to excite the starting compound at other wavelengths such as at its absorption maximum at around 690 nm. The position of the isobestic points and the absorption and fluorescence maxima of the molecules can be influenced by the nature of the environment and in particular the other constituents of the composition containing them. On the other hand, the action of HX probably takes place on the central metal with ejection of the latter and protonation of the two nitrogens at the centre. A resolution of the peaks is then observed. These molecules are particularly suited to compounds of $BX_3$ and HX type. The do not react with compounds of $X_2$ type.

Fluorescein and its derivatives, in particular those used as a stain, can also be used as probe molecules according to the invention. More typically, this is a fluorone derivative comprising an aryl group carbon not involved in the bridging bonds of the central ring and more particularly compounds of formula (IVa) and (IVb):

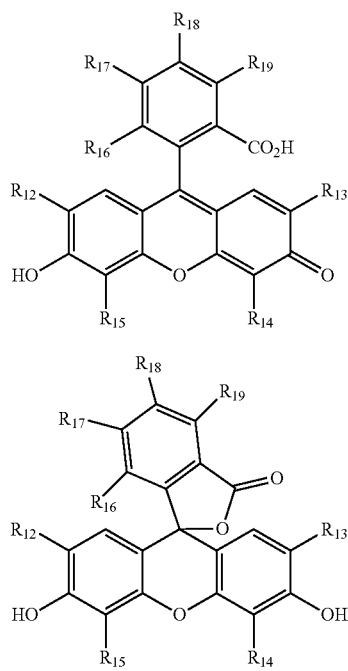

in which:

$R_{12}$, $R_{13}$, $R_{14}$ and $R_{15}$ independently correspond to a H, an alkyl group comprising 1 to 4 carbon atoms, a halogen, an —$NO_2$ group.

$R_{16}$, $R_{17}$, $R_{18}$ and $R_{19}$ independently correspond to a H, a $C_1$-$C_6$ alkyl, a $C_1$-$C_6$ aryl, a halogen, an amine, hydroxyalkyl, an —N═C═S.

The formulae (IVa) and (IVb) correspond to forms which can exist in chemical equilibrium.

Typically the probe molecule is chosen from the following fluorescein derivatives (denomination and CAS number reference): fluorescein "Acid yellow 73" (CAS: 2321-07-5), 6-aminofluorescein (CAS: 51649-83-3), 5-aminofluorescein (CAS: 3326-34-9), 6-carboxyfluorescein (CAS: 3301-79-9), fluoresceinthioisocyanate (CAS: 3326-32-7), fluorescein 27 (CAS: 76-54-0), dinitro fluorescein CAS 24545-86-6, tetra-chloro fluorescein (CAS 6262-21-1), dibromofluorescein "solvent red 72" (CAS: 596-03-2), eosin B "acid red 91" (CAS: 56360-46-4), eosin Y "acid red 87" (CAS: 15086-94-9), eosine-5-thiosemicarbazide (CAS: 1 19881-42-4), erythrosine B "solvent red 114" (CAS: 15905-32-5), erythrosine B isothiocyanate (CAS: 72814-84-7), rose bengal lactone (CAS: 4159-77-7), phloxine B (CAS: 18472-87-2).

For such probe molecules, the spectrophotometric properties measured are in particular absorbance and fluorescence. These probe molecules are characteristic of compounds of $BX_3$ and HX type. They do not react significantly with compounds of $X_2$ type.

Probe molecules from the dyes of the family of triarylmethanes can also be used, in particular dyes from the family of aminotriarylmethanes, particularly the di- and triaminotriarylemethanes, i.e. triarylmethanes bearing on two or three of the rings a nitrogen in a para position of the carbon linking the three rings, more particularly aminotriarylmethanes of formula (V):

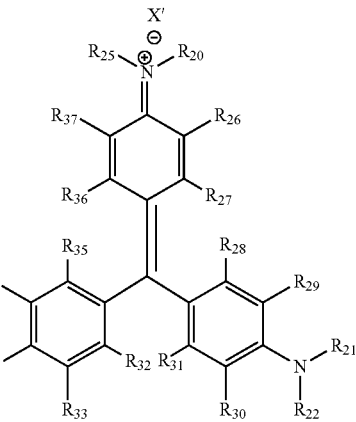

in which:

$R_{20}$, $R_{21}$, $R_{22}$ and $R_{25}$ independently correspond to a H, a carbon-containing chain, and in particular an alkyl radical comprising 1 to 6 carbon atoms and preferably methyl, propyl, butyl, an aryl radical, $R_{26}$, $R_{27}$, $R_{28}$, $R_{29}$, $R_{30}$, $R_{31}$, $R_{32}$, $R_{33}$, $R_{34}$, $R_{35}$, $R_{36}$, and $R_{37}$ independently correspond to a H, a carbon-containing chain, and in particular an alkyl radical containing 1 to 6 carbon atoms, and preferably methyl, propyl, butyl, an aryl radical which can be bridging, an organic function not comprising carbon and typically $SO_3^-$, Z corresponds to a H, an amine of —$NR_{23}R_{24}$ type, an ammonium of —$N^+R_{23}R_{24}R_{54}$ type, with $R_{23}$, $R_{24}$ and $R_{54}$ independently chosen from H, a carbon-containing chain, and in particular an alkyl radical containing 1 to 6 carbon atoms, and preferably methyl, propyl, butyl, an aryl radical, X' is a halogen and preferably F, Cl, Br or I or an organic anion such as oxalate.

Preferably the probe molecule is a hydrophobic compound. Crystal violet (or Paris violet, or gentian violet, or methyl violet) which is used especially in microbiology for staining gram-type bacteria is a particularly useful aminotriarylmethane. This can also be (denomination and CAS number reference) the lactone originating from crystal violet (CAS: 1552-42-7) malachite green G (CAS: 633-03-4), ethyl green (CAS: 71 14-03-6) methyl 2B (CAS: 8004-87-3), methyl 6B (CAS: 548-62-9), methyl 10 B, coomassie (CAS: 6104-58-1) fuchsin (CAS: 569-61-9), methyl blue (CAS:

28983-56-4) new fuchsin (CAS: 3248-91-7), pararosaniline (CAS: 569-61-9), Victoria blue BO (CAS: 2390-60-5).

For such probe molecules, the spectrophotometric properties measured are in particular absorbance and fluorescence. These probe molecules are characteristic of the compounds of $BX_3$, and HX type. The do not react significantly with compounds of $X_2$ type.

Typically, the spectral properties measured in steps (a) and (c) are absorbance, or fluorescence.

It is possible to use different probe molecules simultaneously. It is in this case preferable to use molecules for which the variations of the physico-chemical properties, such as the spectral properties, are different in the presence of the same compound. Thus for example a probe molecule reacting only with compounds of $BX_3$ and $X_2$ type can be used simultaneously with a probe molecule reacting only with compounds of $BX_3$ and HX type for detecting and measuring simultaneously the presence of the different types of compounds. The different probe molecules can be mixed to the extent that they are inert to each other, tests can be carried out beforehand by a person skilled in the art according to the mixture that he intends to use. It is also possible to separate them physically.

The composition can, as seen above, also contain one or more compounds other than the probe molecule.

According to a particular embodiment, the composition comprises a matrix, in which the probe molecule is incorporated. Typically, the matrix is an organic polymer which can be chosen from polysaccharides such as chitosan, cellulose or their derivatives, porous materials based on inorganic polymers, or organic-inorganic hybrids, hydrogels or aerogels. This embodiment is recommended in particular when the probe molecules alone cannot easily be deposited directly and easily preserved on a support, such as those typically used in the context of spectrophotometric measurement such as a glass slide, for example when they are powdery or liquids.

The probe molecule can also be deposited directly on a support by evaporation of the solvent, in this case, the preferred structure of the probe molecule is of polymeric type and corresponds typically to formula (I) in which $R_4$ corresponds to a polysaccharide.

In the case of the matrices of porous materials based on inorganic polymers or organic-inorganic hybrids, the incorporation of the probe molecule in the matrix involves in particular sol-gel chemistry (polycondensation of networks of metallic oxides) and the physico-chemistry of the surfactant phases in solution (self-assembly of micelles in organized structures on the nanoscopic scale).

It is preferable to use porous matrices with pores of small size (diameter <20 Å) in order to increase the specific surface of adsorption of the target pollutant and to increase the probability of reactive collisions between the reagents.

The probe molecule can advantageously be incorporated within a nanoporous sol-gel matrix of metallic oxides. The nanoporous sol-gel matrix of metallic oxides can be prepared from at least one metallic precursor of formula (VI):

in which:

M corresponds to a metal chosen from silicon, aluminium, titanium, zirconium, niobium, vanadium, yttrium and cerium, Y is a halogen, preferably chlorine.

$R_{38}$ and $R_{39}$ independently correspond to an alkyl or aryl radical, i, j and k are integers, such that their sum is equal to the valency of M and that i+j is greater than or equal to 2.

According to a preferred embodiment, the metal M is silicon or zirconium.

According to a particularly preferred embodiment, the metallic precursor is $Si(OMe)_4$ or $Si(OEt)_4$.

Moreover, it is known that the choice of the metallic precursor influences the size of the pores of the matrix and thus the accessibility to the probe molecule of the compounds to be detected. For example, in the case of silicon oxides, the size of the pores reduces with the length of the $R_{38}$ and $R_{39}$ chains, as the chains are overlapped and the porosity reduces. The size of the pores can be increased by incorporating a surfactant which acts as a mould around which form rigid walls of the inorganic polymer, the surfactant then being eliminated by washing. Thus, it is preferable to use matrices prepared from metallic oxides of formula (VI) for which $R_{38}$ and $R_{39}$ are alkyls or alkylamines containing 1 to 6 carbon atoms and preferably methyl or ethyl radicals in order specifically to detect molecules with a diameter less than 6 Å, or propylamine for detecting molecules having a larger diameter (12 Å).

When it is said that the composition contains a probe molecule, it must of course be understood that the composition contains at least one probe molecule, and preferably a quantity of probe molecule sufficient to allow the measurement of the physico-chemical properties of interest under conditions corresponding to the minimum desired detection threshold. Determination of the threshold depends on the detection threshold of the technical means available to the user. Similarly, it must be understood that at least one physico-chemical property of the composition is measured. Similarly, it must be understood that it is possible to detect and/or measure the presence and/or the quantity of one or more gaseous compounds. On reading the description, a person skilled in the art knows in which cases the term "one" means "at least one", or "only one".

In order to carry out measurements of the physico-chemical properties of the composition it is generally desirable, in particular when spectrophotometric or electrical properties are concerned, to deposit the composition on a support suitable for the means of measuring the properties. In the case of spectrophotometric properties this will typically be a solid support which will not interact with the composition and will generally have a flat surface. In the case of electrical properties this will be in particular conductive supports such as conductive polymers or carbon nanothreads or nanotubes. The spectral properties of the support are variable but they are chosen such that they do not interfere with measurement of the spectrophotometric properties of the composition. The substrate is suitable for the spectrophotometric technique which makes it possible to carry out the measurements, this is generally a slide, often transparent to UV and/or visible light, constituted typically of glass, plastic material or quartz used during measurement of the variations of absorption by transmission. When it is required to measure the variations of absorption by reflectance or luminescence, the support can be opaque and also have an incurved surface allowing a better distribution of the light beams for analysis.

Initially in the form of a liquid solution, the composition is typically deposited directly onto the support by various techniques such as depositing a drop of solution and spreading it on the substrate, (Langmuir-Blodgett, spraying, spin coating, dip coating at a constant withdrawal speed, etc. or by evaporation under a partial vacuum. The dip coating process is particularly suitable in the presence of quaternary ammoniums which easily form micelles in particular when they bear long chains, typically $C_{10}$-$C_{22}$. When the composition comprises a matrix which is a cationic polymer such as chitosan, the latter can be solubilized in a solvent then deposited on a suitable substrate by spin-coating or dip-coating. The composition, initially in solid form, can also be deposited directly on the support by sublimation under a partial vacuum.

The gas can be put in solution in a solvent to be brought into contact with the composition during step (b). Preferably, in step (b), the gas is brought into contact with the composition comprising the probe molecule in the form of a gaseous stream.

The second measurement, carried out in step (c), relates to the same property as in step (a), and particularly the absorbance, reflectance or luminescence. In these three cases the variation is linked to a change in the absorbance, reflectance or luminescence of the starting probe molecule or to the appearance of properties linked with the product originating from the reaction of the probe molecule with the gas which has been detected.

According to a particular embodiment, step (d) also comprises the correlation of the variation of said spectral property between steps (a) and (c) to the quantity of gaseous compound of $BX_3$, HX type or $X_2$ type in the gas.

Steps (b) and (c) can be carried out simultaneously. Thus the variation of the spectral property can be monitored over time, and by correlation the quantity of gaseous compound of $BX_3$, HX type or Xj type can be determined.

According to another embodiment, different properties, and in particular the spectrophotometric properties such as the absorbance, reflectance or luminescence are measured in steps (a) and (c).

The means which can be used to carry out the measurements of physico-chemical properties of the composition are those used as standard in the field considered. As regards the spectrophotometric properties, the means used are those which make it possible to carry out optical measurements and in particular measurements of absorbance, fluorescence or reflectance.

Generally the photons can be collected and analysed via a spectrophotometer, a diode strip or also directly by a photomultiplier. In this latter case, the use of narrowband or wideband interference optical filters is be required in order to distinguish the variations of the properties of the probe molecule or/and of the product originating from its reaction with the pollutant. Depending on the property which is measured, the device comprises means of excitation of the probe molecule at a suitable wavelength.

According to a particular embodiment, it is possible to use surface plasmons in order to intensify the variations in the optical properties of the probe molecules. In fact, probe molecules excited by light irradiation close to a thin layer of metal can couple to the surface plasmons and lead to lower detection limits, thus allowing detection or quantification of smaller quantities of gas.

According to another embodiment, the property measured corresponds to the interaction with waves of the Love type. The structural modifications linked to the reaction of the probe molecules with the gas lead in particular to a variation in mass, viscoelasticity, or also dielectric constant which has an effect on the waves of the Love type. This embodiment is generally implemented in the presence of a piezoelectric material which acts as a support or on which it is possible to detect and generate waves of the Love type, typically using interdigital comb electrodes according to a delay line or resonator configuration. The micro-balance devices exploiting the measurements of the variation of resonance frequency of the quartz crystals on which the composition is deposited can also be used in order to quantify the target pollutants which have reacted with these latter.

Once one or more gaseous compounds of $BX_3$, HX or $X_2$ type have been detected, the invention also makes it possible to eliminate them.

A subject of the invention is therefore also a process for trapping gaseous compounds of $BX_3$, HX or $X_2$ type contained in a gas, characterized in that the gas is brought into contact with a composition as defined previously.

It is preferable that the composition comprises a matrix or that the probe molecule has a polymeric nature.

The composition is typically put in a cell which can in particular take the form of an enclosure having any shape whatever, for example parallelepipedic or cylindrical, provided with baffles to extend the contact length or not, provided with an inlet for the gas to be treated and an outlet for the treated gas. The composition can, as stated previously, be deposited on a support which can in particular be arranged in the baffles. The nature of the support, within the context of the elimination of the gas, is not very important, it is of course desirable for it to be chemically inert with regard to the composition. This is in particular a support made of glass, quartz or also plastic materials.

For such a treatment, the porous matrices can be in the form of powders or granules enclosed in a cylindrical tube or also in the form of thin porous films deposited on the walls of a cylinder, it being possible to carry out the deposition in particular by evaporation. Depending on the pollutant content to be treated, it is possible to modify the thickness of the film or the quantity of powders or granules and the concentration of the probe molecule.

It is possible to treat several pollutants by incorporating several specific probe molecules.

The quantity of gas trapped corresponds at most to the quantity of probe molecule(s) present in the composition. Thus, for example, for a composition comprising one kilogram of porous matrix with a probe molecule weight content of 5 to 10%, according to the chosen probe molecule it is possible of treat 5,000 to 11,000 m$^3$ of gaseous effluent containing 1 ppm of $BX_3$, HX or $X_2$. Depending on the gas content (>1 ppm or <1 ppm) in the stream, lower or higher volumes can be treated.

A gas suction device is advantageously used to bring large quantities of gas to be treated into contact with the probe molecules.

The cell is in particular designed to treat a flow rate of at least 1 liter of gas per hour, in particular at least 10 liters of gas per hour and preferably at least 100 liters of gas per hour. In general a volume to be treated of 5,000 to 11,000 m$^3$ corresponds to one month of use. As regards the flow rate, higher flow rates can of course be envisaged, 100 liters of gas per minute in order to treat a few m$^3$ in 1 to 2 hours.

In particular, the cell can be a tube. Depending on the flow rate of gas to be treated, it is possible to modify the diameter and length of the tube.

With Ms15, the reaction is reversible. The tube can be pumped under vacuum in order to regenerate Ms15.

It is possible to monitor the saturation of the probe molecules by carrying out measurements of their physico-chemical and particularly spectrophotometric properties, as stated above.

In order to implement the above processes, the inventors have also developed novel materials capable of reacting with a component of $BX_3$, HX or $X_2$ type.

This is why a further subject of the present invention is also a material capable of reacting with at least one compound of $BX_3$, HX or $X_2$ type in gaseous form comprising, or constituted by, a porous matrix containing at least one probe molecule as defined above. The porous matrix is typically constituted by a matrix of inorganic polymers or organic-inorganic hybrids prepared according to the sol-gel process.

The invention also relates to a process for the preparation of the above material comprising the following steps:

(a) preparation of a preferably sol-gel porous matrix, and
(b) incorporation in said porous matrix of a probe molecule as defined above, in order to obtain the desired material.

The porous matrix according to the invention is preferably prepared according to a sol-gel process. Under the generic name "sol-gel process", techniques are grouped together which make it possible to obtain inorganic matrices or organic-inorganic hybrids by simple polymerization of metallic precursors, including in particular metallic oxides, at temperatures close to ambient temperature (20 to 35° C.). The chemical reactions, i.e. hydrolysis and condensation, on which sol-gel processes are based, are initiated when the metallic precursors are brought into the presence of water. The solvents of the precursors can be chosen in particular from alcohols, ethers including THF or $CH_2Cl_2$, $CHCl_3$. Thus the hydrolysis of the metallic oxides takes place first, then the condensation of the hydrolysed products leads to gelling of the matrix. The solvent can also correspond to a mixture of the solvents mentioned previously.

Surfactants can moreover optionally be used either to induce a structuring of the porous matrix and to form pores of a size which can be modified, or to solubilize a weakly polar probe molecule which is not very soluble in the mixture of precursors and solvent, such as a mixture of alcohol and water, or for both properties.

According to a preferred embodiment of the process according to the invention, the metallic precursor is an metallic oxide, the step of preparation of the sol-gel porous matrix (a) comprises a step of hydrolysis of at least one metallic oxide, said hydrolysis step being preferably carried out in the presence of an organic solvent such as an alcohol like methanol or ethanol.

During the condensation, the hydrolyzed products react together to form polymers which continue to grow until a three-dimensional polymer network is obtained. Firstly, the metallic oxide clusters remain in suspension without precipitating, this is the sol. These clusters progressively occupy an increasingly large volume fraction. The viscosity then becomes significant and finally the liquid gels into a matrix. The matrix thus obtained is therefore constituted by a polymeric network which has a porosity that can be varied according to requirements.

The diameter of the pores of the sol-gel matrix can also be adapted by selecting particular metallic oxides. For example the metallic oxides of formula (VI) for which $R_{38}$ and $R_{30}$ are alkyls, preferably methyl or ethyl radicals, make it possible to generate matrices, the pores of which have a reduced diameter. Those for which $R_{38}$ or $R_{39}$ is a aminoalkyl, preferably aminopropyl, making it possible to generate matrices the pores of which have large diameters.

According to a particular embodiment, the step of preparation of the sol-gel matrix (a) and that of incorporation of at least one probe molecule (b) are carried out simultaneously, in fact the conditions of preparation are sufficiently gentle for the probe molecules to be incorporated in the sol-gel matrix without being altered.

It is desirable that an additional homogenization and/or drying step is carried out. The drying step allows, among others, evaporation of the solvent(s), such as the water and alcohols, present in the matrix. Advantageously, the incorporation of at least one probe molecule is provided before the homogenization step, preferably during the hydrolysis step.

According to another preferred embodiment, the incorporation of at least one probe molecule can be carried out in the porous matrix also by impregnation in solution or in vapour phase according to techniques well known to a person skilled in the art, including in particular sublimation.

For the implementation of the processes described previously, the composition presented above and in particular the material according to the invention can be integrated into devices, in particular sensors, generally based on the detection of spectrophotometric properties.

The present invention thus also relates to a device or in particular a sensor for compounds of type $BX_3$, HX or $X_2$ in gaseous form characterized in that it comprises at least one material or a composition, preferably in the form of a matrix, according to the invention.

In order to increase the area of the exchange surface it is preferable that the composition comprises a matrix if the probe molecule that it contains does not itself form a matrix, when a sensor is used.

According to a preferred embodiment, a sensor comprises a material or a composition, according to the invention, deposited on a suitable substrate, preferably in the form of a thin film on a transparent substrate. The substrate can be chosen from those used as standard in the field of spectrophotometric analysis, including in particular slides or plates made of glass, mica, quartz or fluospar.

Typically, the deposit is carried out according to techniques well known to a person skilled in the art, including, in particular, dip coating, spin coating, by spraying (liquid or gas), deposition and spreading of a drop. Advantageously, the deposition is carried out by dip coating when possible. This is particularly the case during the preparation of the materials according to the invention. A person skilled in the art will adapt the speed of withdrawal of the substrate of deposit to the material deposited, preferably a speed close to 25 $mm.min^{-1}$.

Dip coating can be done at ambient temperature (22-25° C.) with a relative humidity of the air comprised between 15 and 50%.

For increased efficiency, slides or plates are installed in a parallel fashion as in an accumulator-type battery.

According to another preferred embodiment which can be used in particular when the physico-chemical properties are spectral properties, the devices or sensors according to the invention intended for the detection include at least one light excitation source and one collector.

They are in particular composed of a first compartment, a second compartment and a screen. The gas is fed into the sensor via a specific inlet, then passes through a thermostat which makes it possible to monitor the temperature, as well as a particle filter. A micropump system, which can be located either upstream or downstream of the material, makes it possible to accelerate the diffusion of the gas as far as the probe molecules, which may or may not be enclosed in a material according to the invention.

It is useful that the sensor is equipped with a measurement system making it possible to determine the volume of gas having passed through the inlet. It should be made clear that the composition, which corresponds in particular to the material shown above, is protected from the outside environment by a protective envelope in a leaktight manner by means of a seal, for example an O-ring. If the gas contains a compound of $BX_3$, HX or $X_2$ type, the latter will react with the corresponding probe molecules contained in the composition.

The reaction with the probe molecule is detected after light excitation by a collector and read on the screen.

Advantageously, the light source is constituted by a deuterium or halogen lamp or a light-emitting diode, and the collector is constituted by a diode strip or a low-voltage photomultiplier.

When the detection process is based on a variation in the absorbance of the doped film, it is preferable to use a system composed of two thin doped films each deposited on a reflective substrate in order to optimize the absorption of the light source by the probe molecules. As the photons bounce many times on the walls covered with films, they are strongly absorbed by the probe molecules contained in the composition. When the probe molecules are fluorescent or when the product of the reaction between the probe molecule and the gas results in the formation of a fluorescent compound, a metallic layer of aluminium or silver can be deposited on the substrate in order to create resonance plasmons in the excitation wavelength range of the probe molecule or enhance the product of reaction in order to intensify the fluorescence of these compounds. A gas outlet is provided within the context of this sensor. Miniaturized devices or sensors are preferred.

It is desirable that the device or sensor comprises moreover a support for the composition, more particularly a support suitable for the detection process. Advantageously, the device or sensor also comprises a system for accelerating the diffusion of the medium to be analysed, particularly a gaseous medium. Preferably, the system for accelerating the diffusion of the gas is a pneumatic system such as a piston, a delivery pump or a micropump. Such a system is particularly useful in the case of a pollution control device. Direct optical transduction sensors are thus especially envisaged by the invention.

The sensor can also be a multiple sensor, or multi-sensor, making it possible to detect different gases simultaneously and determine their concentration. For this purpose it is possible to use one or more compositions comprising one or more types of probe molecules reacting with different compounds. The different compositions can be mixed in the same film or placed on the same support or also on different supports. Compositions comprising the different probe molecules can be installed in the same compartment or different compartments.

The material according to the invention has numerous advantages which allow it to be used in metrology of halogenated compounds as well as in pollution control.

Due to its preparation process, the material according to the invention is nanoporous and therefore provides a very large specific surface area for adsorption. This structural characteristic is even more significant in the context of the pollution control device. The material according to the invention can be implemented in processes for the detection and/or quantification and/or trapping of halogenated compounds whatever the conditions, including in particular a high level of ambient humidity.

Finally, compositions, such as the material, according to the invention can easily be integrated with a sensor or a device allowing the direct and simple in situ detection of halogens, halogenated acids or gaseous boron halides. Advantageously, sensors can be used in a network and to permanently ensure the quality control of an environment at high risk of contamination by boron halides. The devices or sensors can also be combined with a visual or audible alarm which is triggered when the boron halide content in the environment to be tested reaches a certain critical threshold.

The preferred conditions of implementation of the process for detecting a gaseous compound of $BX_3$, HX or $X_2$ type within a gas described above are also applicable to the other subjects of the invention mentioned above, in particular to the trapping process.

The invention will be understood more accurately from the attached figures and the following illustrative embodiments.

FIG. 1 represents different probe molecules (Ms1 to Ms 15).

FIG. 2 corresponds to the diagram of a sensor according to the invention.

FIG. 3 represents a top view of the compartment of a sensor according to the invention.

FIG. 4 corresponds to a cross-section of the compartment comprising a material according to the invention.

Figure 3:
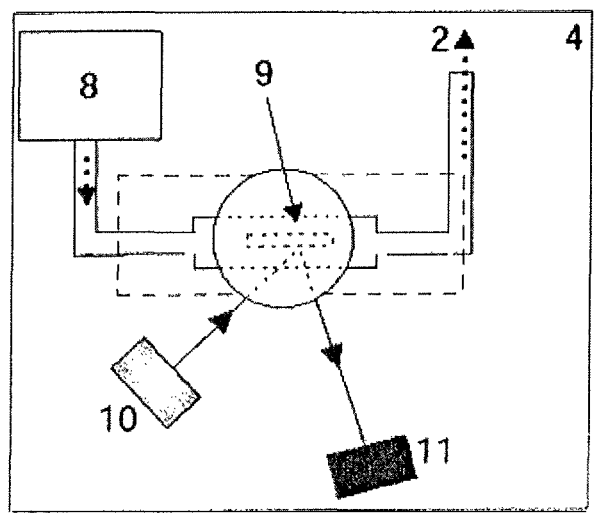

As represented in FIG. 3, devices or sensors which can be used in the invention intended for the detection incorporate at least one excitation light source (10) and one collector (11).

Figure 1:
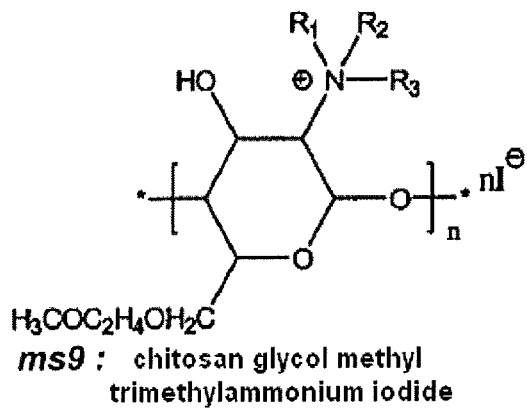
Figure 1:
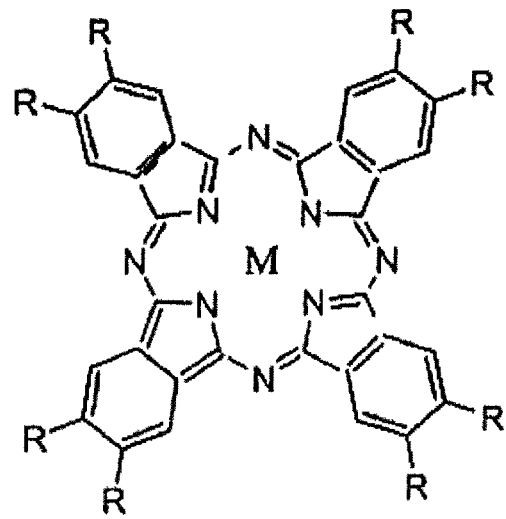
Figure 1:
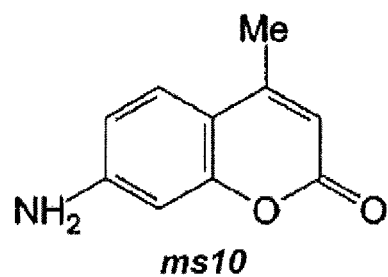
Figure 1:
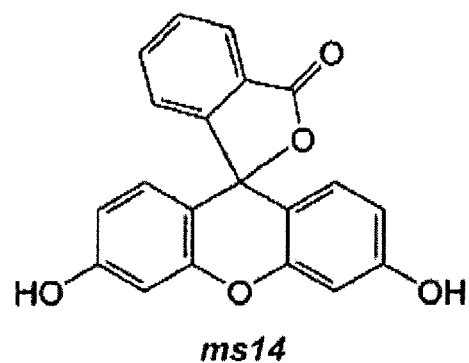
Figure 1:
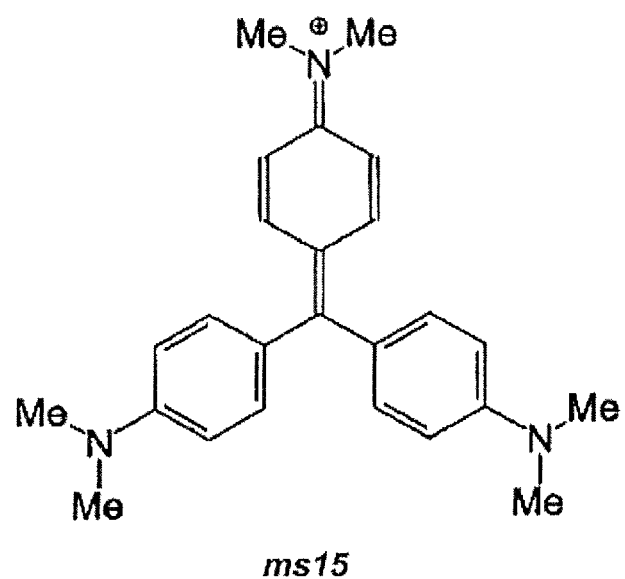
Figure 2:
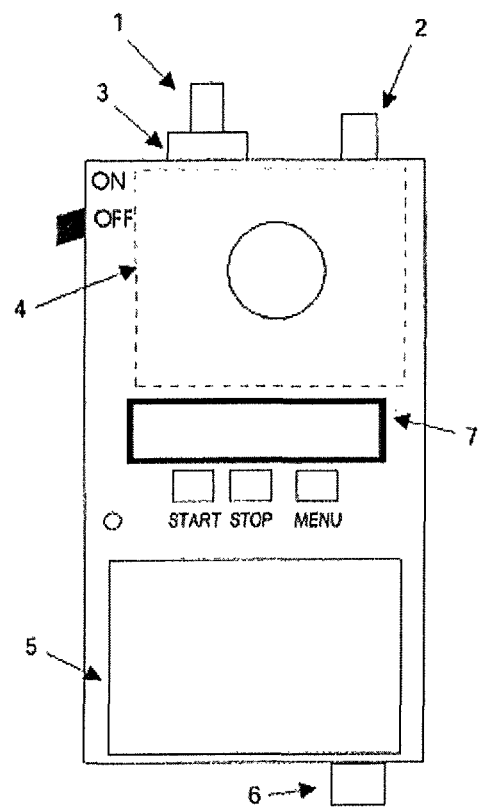

They are in particular, as represented in FIG. 2, composed of a first compartment (4), a second compartment (5), and a display screen (7). The gas can be introduced into the sensor through a specific inlet (1) then passes through a thermostat which makes it possible to control the temperature as well as a particle filter (3). A micro-pump system (8), which can be situated either upstream or downstream of the material, makes it possible to accelerate the diffusion of the gas as far as the probe molecules, which may or may not be enclosed in a material (9) according to the invention.

Figure 4:
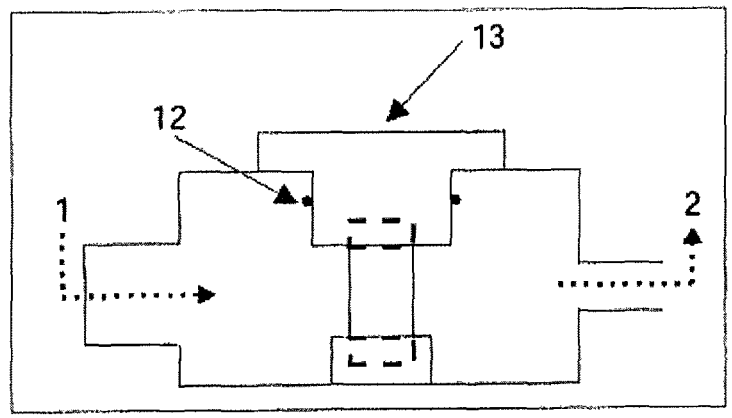

The composition (9), which corresponds in particular to the material presented above, is protected from the outside environment by a protective envelope (13) in a leaktight manner by means of a seal for example an O-ring (12) as represented in FIG. 4. If the gas contains a compound of $BX_3$, HX or $X_2$ type, the latter will react with the probe molecule or molecules contained in the composition corresponding to it.

The reaction with the probe molecule is detected after light excitation (10) by a collector (11) and read on the screen (7).

In the above example, the light source is constituted by a deuterium, halogen lamp or light-emitting diode, and a diode-strip collector.

Figure 5:
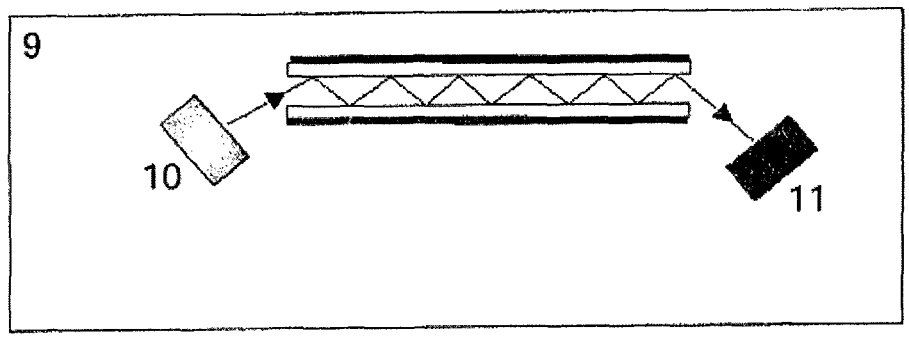
FIG. 5 represents a detection system integrated into a sensor comprising two films of the material.

When the detection method is based on a variation in absorbance of the doped film, it is preferable to use a system comprising two doped thin films each deposited on a reflective substrate in order to optimize the absorption of the light source by the probe molecules. As the photons bounce many times on the walls covered with films, they are strongly absorbed by the probe molecules contained in the as represented in FIG. 5. A gas outlet (2) is provided in the frame of this sensor. Miniaturized devices or sensors are preferred.

In order to illustrate the invention, experiments are presented hereafter which were carried out either with the reagents in solution, or in solid medium (film deposited on substrate) under reduced pressure of gaseous pollutant or also under a gaseous mixture stream constituted by nitrogen and considered pollutants ($BX_3$, HX or $X_2$) in variable concentrations.

In solid medium, the probe molecules can be incorporated in a matrix or deposited on a substrate from a solution. Considering the health and economic challenge that they represent for the electronics industry, the compounds for which detection is illustrated are $BCl_3$, $BF_3$, HCl and $Cl_2$.

Due to the ease of implementation of the spectral measurements and easy accessibility of the means for measurement of the spectrometric properties, the physico-chemical properties of the compositions/probe molecules, the variations of which are illustrated here, are spectrophotometric properties. The spectrophotometric measurements were carried out either with a UNICAM UV-visible spectrophotometer, or with an OCEAN OPTICS miniature spectrophotometer.

The products necessary for implementation of the examples were obtained commercially; no additional purification was carried out.

1. Preparation of the Composition a) Certain probe molecules were used directly, without their being incorporated in a matrix. This applies in particular to Ms9, one of the chitosan derivatives which forms a matrix by itself.

b) Certain probe molecules (such as Ms14, fluorescein, Ms11, magnesium phthalocyanine, Ms15, crystal violet) or mixtures of probe molecules (such as Ms13+Ms15) were used after simple deposition on a quartz slide by evaporation of a solution thereof in ethanol.

c) Matrices containing probe molecules were prepared from silicon tetraalkoxides according to the technique of the sol-gel process as known in the art.

Thus, $Si(OMe)_4$ (or TMOS) was hydrolyzed under stirring in the presence of ethanol at a neutral pH; the mixture is in the following proportions $TMOS/EtOH/H_2O=1/4/4$ or 8.38/10.13/3.96 g.

During the hydrolysis and condensation of the silicon precursors, one or more probe molecules were added to the solution. After a maturation time which can range from a few minutes to several days, a thin mesoporous, optionally nanostructured, film containing the probe molecule(s) is obtained by dipping then withdrawing a support of the solution. A preferred support is a quartz slide and a preferred deposition protocol uses constant dipping and withdrawal speeds.

The probe molecules Ms1 to Ms4 correspond to a first family of probe molecules. These are alkali metal halides. These molecules were selected for their availability, low cost and their ease of use.

Five probe molecules (Ms5 to Ms9) illustrate the use of quaternary ammonium halides. Ms5 and Ms7 are both probe molecules and structuring agents capable of inducing the formation of nanostructured porous matrices. For Ms5 for example, the shape of the pores (in this case spheres 48 Å in diameter) is imposed by the relative concentrations of the various constituents of the sol (acid pH, $TEOS/EtOH/H_2O/HCl/Ms5$ mixture=1/20/5/0.004/0.1).

Ms6 and Ms8 were also used with the sol-gel type matrices.

Ms9 forms an organic polymer matrix.

FIGS. 6 to 11 illustrate the spectra corresponding to the reactions between these various alkali metal halides and ammonium halides and $BF_3$, $BCl_3$ and $Cl_2$.

Ms10 corresponds to a coumarin derivative. These probe molecules react effectively in solution with $BF_3$, $BCl_3$, HCl by forming the protonated or complexed coumarin the absorption spectrum of which is very different from the initial spectrum (see FIGS. 12 and 13). The coumarins do not react with $X_2$.

The probe molecules Ms11, Ms12 and Ms13 correspond to the phthalocyanines.

The probe molecule Ms14 is fluorescein. This will serve as an example to illustrate the detection of $BF_3$, $BCl_3$ and HCl in solution.

The probe molecule Ms15 is crystal violet. This molecule forms part of the family of the triarylmethanes.

2. Detection of Compounds of $BX_3$, HX or $X_2$ Type

A physico-chemical property which can be detected by an analysis technique was determined beforehand for each of the above probe molecules.

| Example No. | Probe molecule | Physico-chemical property | Pollutant | Nature of the variation |
|---|---|---|---|---|
| 1 | Ms1 (NaI) | Absorbs between 190 and 250 nm, Peak at 220 nm | $BX_3, X_2$ | New absorption band 250-450 nm. 2 peaks 288 and 365 nm |
| 2 | Ms2 (KI) | Absorbs between 190 and 250 nm, Peak at 220 nm | $BX_3, X_2$ | New absorption band 250-450 nm. 2 peaks 288 and 365 nm |
| 3 | Ms3 (KBr) | Absorbs between 190 and 220 nm, Peak at 192 nm | $BX_3, X_2$ | New absorption band 230-370 nm. 1 peak 266 nm |
| 4 | Ms4 (NaCl) | Absorbs below 200 nm | $BX_3, Cl_2, F_2$ | New absorption band 220-270 nm. Peak 256 nm |
| 5 | Ms5 (CTAB) | Absorbs between 190 and 220 nm, Peak at 192 nm | $Cl_2, BF_3, F_2$ | New absorption band 230-370 nm. 1 peak 266 nm Disappearance of the absorption band of Ms5 |
| 6 | Ms6 $(Bu)_4N^+I^-$ | Absorbs between 190 and 250 nm, Peak at 220 nm | $BX_3, X_2$ | New absorption band 250-450 nm. 2 peaks 288 and 365 nm |
| 7 | Ms7 (dibrominated) | Absorbs between 190 and 220 nm, Peak at 192 nm | $BCl_3, Cl_2, BF_3, F_2$ | New absorption band 230-370 nm. 1 peak 266 nm Disappearance of the absorption band of Ms5 |
| 8 | Ms8 Monoiodized | Absorbs between 190 and 250 nm, Peak at 220 nm | $BX_3, X_2$ | New absorption band 250-450 nm. 2 peaks 288 and 365 nm |
| 9 | Ms9 chitosan | Absorbs between 190 and 250 nm, Peak at 220 nm | $BX_3, X_2$ | New absorption band 250-450 nm. 2 peaks 288 and 365 nm |
| 10 | Ms10 Coumarin | 2 absorption bands 190-270 and 270-400 nm. Position of the peak depends on the coumarin Fluoresces in the visible range between 380 and 500 nm, position of the peak depends on the coumarin | $BX_3$, HX | Disappearance of the band centred at 350 nm and appearance of 2 new absorption bands between 230 and 330 nm with peaks at 270 and 310 nm Disappearance of the fluorescence band of the probe molecule |
| 11 | Ms11 MgPc | Absorbs in the visible range between 550 and 780 nm Fluoresces between 700 and 1200 nm | $BX_3$, HX | Shift of the absorption band towards the red Shift of the fluorescence spectrum into the red |
| 12 | Ms12 $Si(CH_3)_2Pc$ | Absorbs in the visible range between 600 and 690 nm, peak at 662 nm in EtOH Fluoresces between 660 and 800 nm | $BX_3$ HX | Slight bathochromic shift of the absorption band Disappearance of the absorption band of Ms12 and appearance of a new band centred at 682 nm Bathochromic shift of the fluorescence band Disappearance of the fluorescence of the probe molecule and appearance of a new fluorescence shifted into the red |
| 13 | Ms14 Fluorescein | Absorbs in the visible range between 420 and 550 nm Fluoresces between 475 and 750 nm | $BX_3$, HX $BX_3$, HX | Disappearance of the absorption bands of Ms14 and appearance of a new band shifted towards the blue with a peak centred about 450 nm Disappearance of the fluorescence band of Ms14 |
| 14 | Ms15 Crystal violet | 2 absorption bands centred at 300 and 580 nm Fluoresces between 600 and 800 nm | $BX_3$, HX | Disappearance of the 2 UV and visible absorption bands of Ms15 and appearance of two new absorption bands centred at 430 and 660 nm Disappearance of the fluorescence band of Ms15 |
| 15 | Ms13 + Ms15 (BIC) | Absorption band between 490 and 720 nm Fluoresces between xxx and xxx nm | $BX_3$, HX $BX_3$, HX | Disappearance of the band of the probe molecule and appearance of a new band at 440 nm Disappearance of the fluorescence band of the probe molecule |

Each of the samples was then exposed for a variable period to a gas to be detected, mainly comprising pure compound of $BX_3$, HX or $X_2$ type under reduced pressure, to a gaseous mixture of nitrogen containing the pollutant at levels which were varied (40 ppb to 500 ppm) or by bringing into contact with a solution through which the gas is bubbled.

The following experiments were carried out:

| FIG. no. | Probe molecule | Compounds tested | Vector gas, reduced pressure or bubbling (liquid) | Pressure (torr) | Duration |
|---|---|---|---|---|---|
| 7 | MS1 | $Cl_2$ (400 ppb) | $N_2$ 50 mL·min$^{-1}$ | 760 | Spectrum collected every 5 min |
| 6 | MS2 | $BCl_3$ (liq) | liquid MeOH | — | Spectrum collected every 20 min |
| 9 | MS5 | $BF_3$ (gas) | reduced pressure | 0.1 to 0.6 | Spectrum collected at equilibrium |
| 11 | MS7 | $Cl_2$ (200 ppb) | $N_2$ 250 mL·min$^{-1}$ | 760 | Spectrum collected every 40 sec |
| 10 | MS8 | $Cl_2$ (40 ppb) | $N_2$ 250 mL·min$^{-1}$ | 760 | Spectrum collected every 10 min |
| 8 | MS9 | $BCl_3$ (gas) | reduced pressure | 0.48 | 10 hours |
| 12 | MS10 | $BF_3$ (liq) | liquid MeOH | — | 5 min after addition of $BF_3$ |
| 13 | MS10 | HCl (45 ppm) | $N_2$ 50 mL·min$^{-1}$ | 760 | Spectra collected every 30 sec, then every 10 min. monitored over 1 hour 10 min. |
| 14 | MS11 | $BF_3$ (liq) | liquid EtOH | — | 5 min after each addition of $BF_3$ |
| 15-16 | MS11 | $BF_3$ (gas) | reduced pressure | 1 | Monitoring of spectrum over 3700 min |
| 17 | MS12 | $BF_3$ (liq) | liquid EtOH | — | Monitoring of spectrum 5 min and 1 hour |
| 18 | MS12 | HCl | $H_2O$ | — | Monitoring of spectrum after the addition of HCl |
| 19 | MS14 | $BF_3$ (liq) | liquid MeOH | — | Monitoring of spectrum after the addition of $BF_3$ |
| 20 | MS14 | $BCl_3$ (gas) | reduced pressure | 0.48 | Monitoring of spectrum over 2 hours, exponential decline |
| 21 | MS15 | $BF_3$ (liq) | liquid MeOH | — | Monitoring of spectrum after the addition of $BF_3$ |
| 22 | MS15 | HCl (gas) | reduced pressure | 4 | Monitoring of spectrum over 1 hour |
| 23 | BIC | $BF_3$ (gas) | reduced pressure | 2 | Monitoring of spectrum over 16 hours |
| 24 | BIC | HCl | liquid EtOH | — | Monitoring of spectrum |

Figure 6:
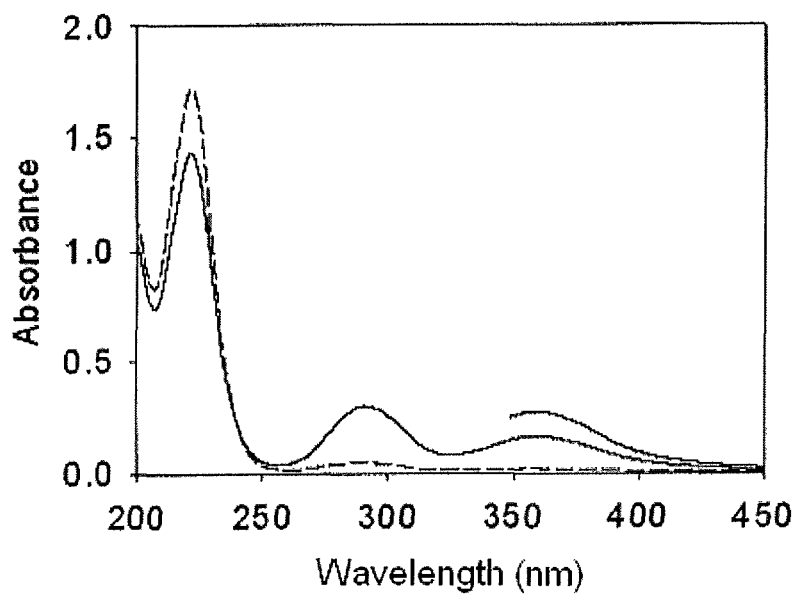
FIG. 6 represents the absorption spectrum of KI in methanol and its development during the addition of $BCl_3$ as a function of time.

FIG. 6 shows the spectral variations, using absorption spectroscopy, resulting from the reaction of $Ms_2$ with $BCl_3$ in methanol.

A $5 \cdot 10^{-5}$ mol·L$^{-1}$ solution of Ms2 in methanol to which an aliquot of a concentrated solution of $BCl_3$ is added so that the concentration of $BCl_3$ is in excess with respect to that of Ms2 ($1.3 \cdot 10^{-3}$ mol·L$^{-1}$). An initial absorption spectrum of the solution of Ms2 is collected (curve in dotted line) before the addition of $BCl_3$. A spectrum is collected every 20 minutes after the addition. The disappearance of the absorption band of MS2 centred at 220 nm and the appearance of two new absorption bands centred at 288 and 358 nm are observed. From the measurements of variation in the absorbances at 288 and 358 nm as a function of the concentration of $BCl_3$, it is possible to plot calibration curves which serve for the quantitative measurement of $BCl_3$ in solution.

Figure 7:
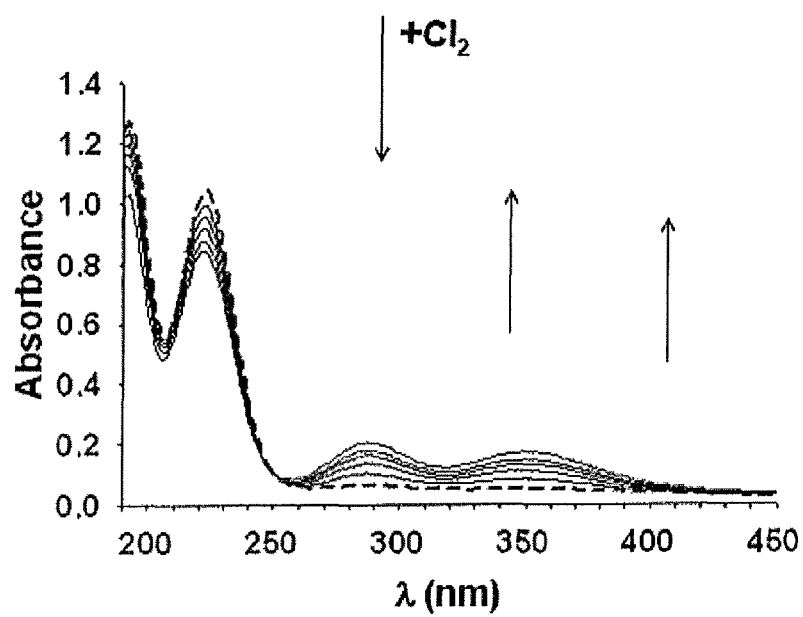
FIG. 7 represents the absorption spectrum of NaI in a porous matrix and its development when the matrix is exposed to a gaseous mixture containing chlorine.
Figure 8:
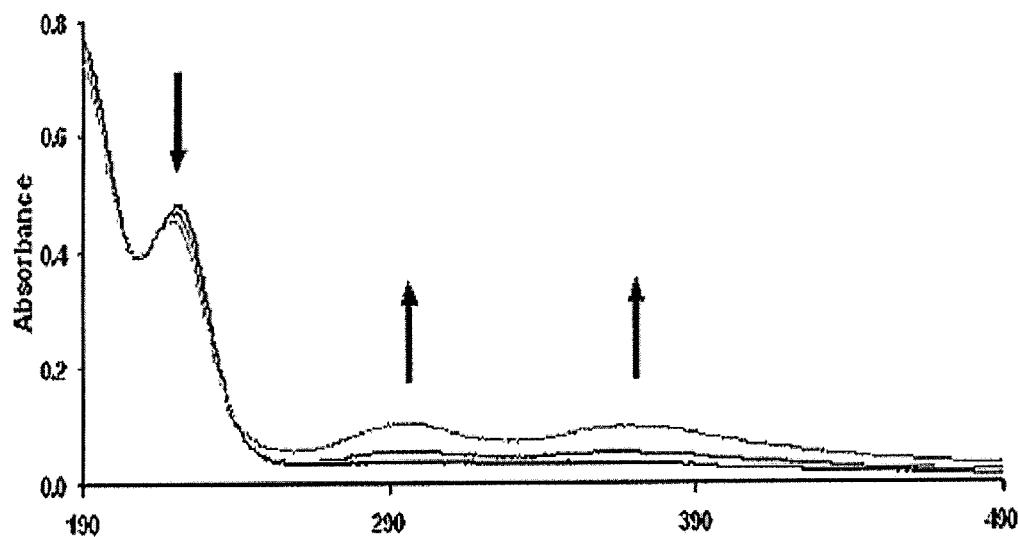
FIG. 8 represents the absorption spectrum of a film of trimethylammonium methylglycol chitosan iodide and its development when the film is exposed under reduced pressure to $BCl_3$.
Figure 9:
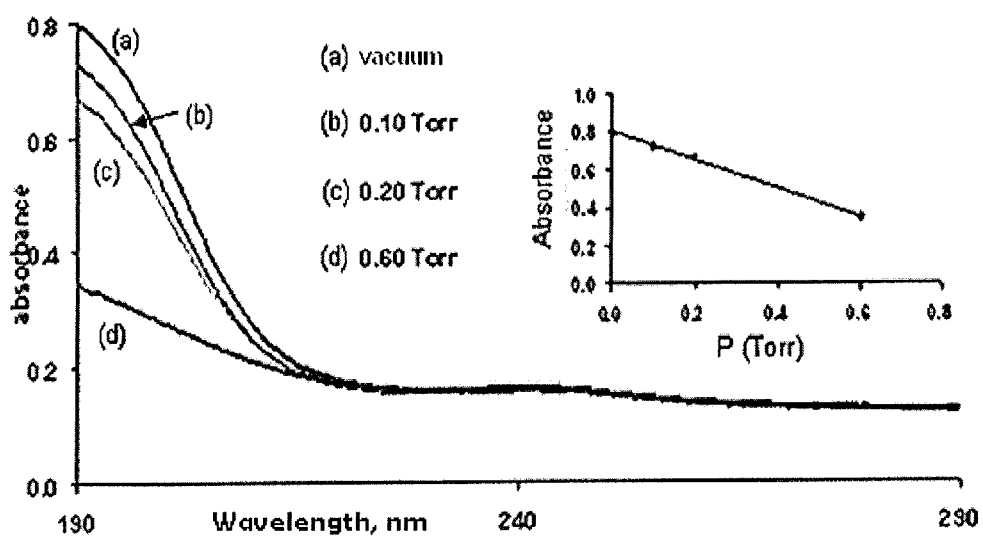
FIG. 9 represents the absorption spectrum of CTAB $(C_{15}H_{33})(Me)_3N^+,Br^-$ in a porous matrix and its development when the matrix is exposed to gaseous $BF_3$; the variation in absorbance as a function of the pressure introduced (in Torr) is represented in the inset.
Figure 10:
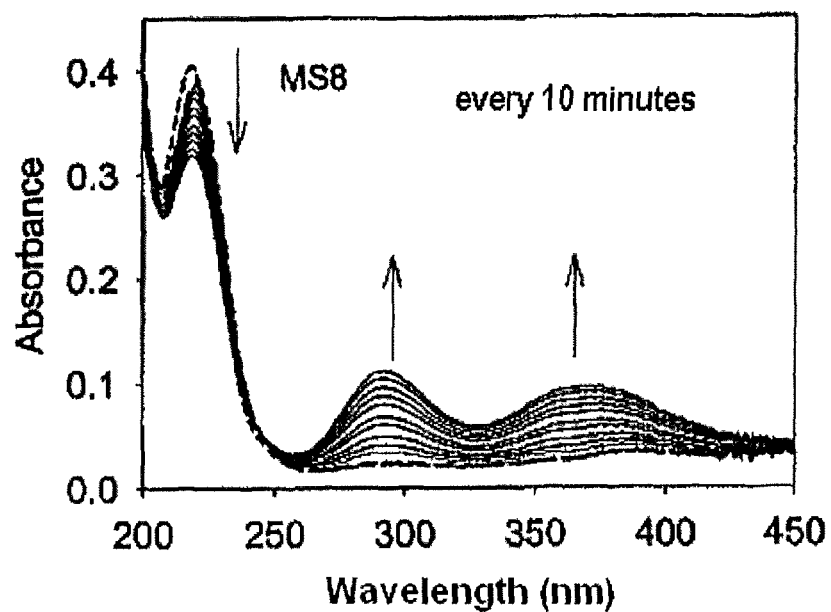
FIG. 10 represents the absorption spectrum of $HO(CH_2)$ $(Me)3N^+, I^-$ in a porous matrix and its development when the matrix is exposed to gaseous $Cl_2$ (40 ppb).
Figure 11:
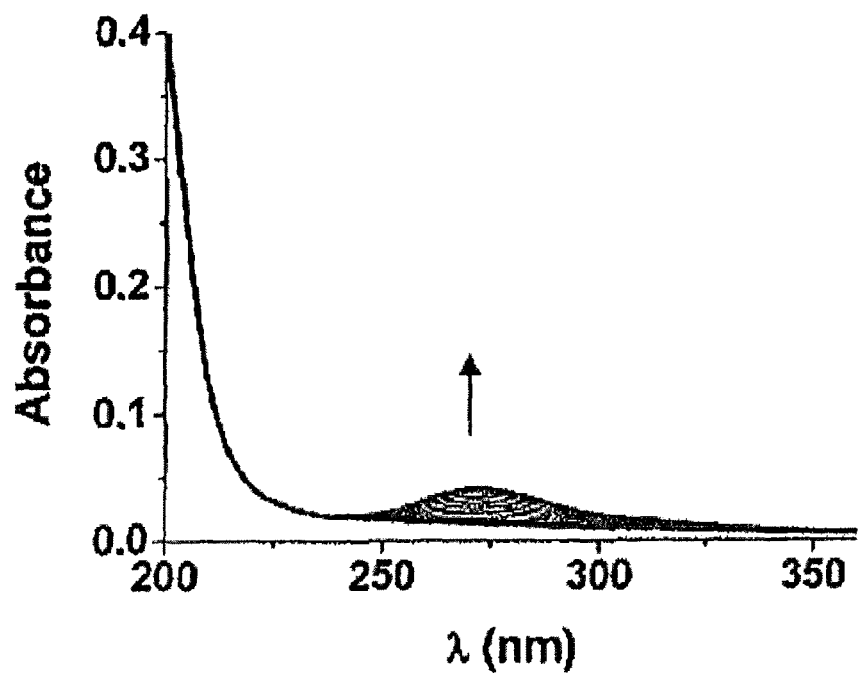
FIG. 11 represents the absorption spectrum of decamethonium dibromide $^-Br5(Me)3N^+—(C_{10}H_{22})—N^+(Me)_3Br^-$ in a porous matrix and its development when the matrix is exposed to gaseous $Cl_2$ (200 ppb).

FIG. 7 shows the variations in absorbance of MS1 incorporated in a porous matrix produced according to the sol-gel process when it is exposed to a stream of $Cl_2$ (gas). The doping of the porous matrix is carried out according to the one-pot method used in the sol-gel process. Ms1 is directly incorporated in the solution of precursors the composition of which is: TMOS/OH/$H_2O$/MS1=1/4/4/0.11.

The mixture is stirred under ultrasound for 5 minutes. Porous films doped with Ms1 are prepared by dipping quartz substrates in the solution and withdrawing them at a constant speed (9.6 cm min−1). When the film is exposed to a stream (50 mL·min−1) of gaseous mixture containing 400 ppb of $Cl_2$, the reduction of the absorption band of Ms1 centred at 220 nm is observed, to be replaced by the appearance of two new bands centred at 288 and 350 nm. In the same manner, from the measurements of the variation in absorbance at 288 and 350 nm as a function of the $Cl_2$ content of the gaseous stream and for the same flow rate, it is possible to plot calibration curves from which it is possible to determine the $Cl_2$ content of a gaseous stream by exposing a film doped with Ms1 to this stream.

Four examples of reactivity of the probe molecules of ammonium halide type are shown in FIGS. 8 to 11. Ms5, Ms7 and Ms8 are at the same time structuring agents which make it possible to obtain nanostructured, porous, thin films since Ms9 serves both as a probe molecule and as matrix because Ms9 is a polymer.

Ms5 is incorporated in the form of micelles in mesoporous thin films of 3D-hexagonal structure based on organic-inorganic hybrid polymers of silicon according to a protocol known from the literature [Bourgeois. A.; Brunet Bruneau, A.; Fisson, S.; Demarets, B.; Grosso, D.; Cagnol. F.; Sanchez, C.; Rivory, J., Thin Solid Films. (2004), 447-448, 46-50] and described below.

The first step involves preparing a prehydrolyzed solution $S_p$ of molecular precursors containing tetra-ethoxy silane (TEOS), ethanol, water and hydrochloric acid in the molar proportions: TEOS:EtOH:$H_2O$:HCl=1:3:1:5.10$^{-5}$. This mixture is heated under reflux for one hour. A second solution containing ethanol, acid water (0.055 mol·L$^{-1}$ HCl) and MS5 is then added to the solution $S_p$. The final composition of the sol is then given by the following molar proportions: TEOS: EtOH; $H_2O$:HCl:MS5=1:20:5:0.004:0.10. This mixture is stirred for 72 hours at ambient temperature in a hermetic container. The thin films of the mesoporous material are obtained by depositing a fine layer of the sol on a quartz slide by the dip-coating method with withdrawal at a constant speed. The withdrawal speed applied in most cases is 3 mm. s$^{-1}$. During the deposition, the humidity level in the chamber of the device is fixed at a value comprised between 40% and 60%. The film is heated with an infrared heating unit for 15 minutes at a moderate temperature (160° C.) in order to stiffen the inorganic network without destroying the Ms5. The micelles of Ms5 are contained in spherical pores with an average diameter of 4.5±0.5 nm, arranged according to a 3D-hexagonal structure and separated from each other by a porous wall of inorganic polymer with a thickness of 2.5±0.5 nm. During the exposure of the thin film to $BF_3$, the pollutant molecules diffuse rapidly via the porous network of the polymer towards the Ms5 micelles. The detection of $BF_3$ is optical. The absorbance of Ms5 is measured in the UV. The latter reduces quantitatively with the addition of gaseous $BF_3$ (see FIG. 9).

Various organized structures of Ms5 micelles can be obtained depending on the proportions of TEOS and Ms5 such as the cubic (0.1<MS5/TEOS<1), or mixed cubic-hexagonal or also lamellar structure. In all cases, the Ms5 micelles react with the $BF_3$ in the same way. Only the initial absorbance of Ms5 varies with its initial concentration.

Ms7 is also a structuring agent. Due to the terminal position of the two ammoniums, which makes it possible to obtain thin films with a lamellar structure.

The protocol used for the preparation of mesoporous thin films is identical to that presented for Ms5, the proportions and the values of the parameters indicated are similar. The film obtained is heated with an infrared heating unit at a moderate temperature (160° C.) for 15 minutes in order to stiffen the inorganic network without destroying the probe molecules. During the exposure of the thin film doped with Ms7 to $Cl_2$, the molecules of pollutant diffuse rapidly via the porous network of the polymer towards Ms7. The detection of $Cl_2$ is optical. The absorbance of Ms7 is measured in the UV. The latter reduces quantitatively with the addition of gaseous $Cl_2$ (see FIG. 11).

The absorption spectrum of Ms7 is similar to that of Ms5. An absorption in the UV is observed with a maximum centred towards 192 nm. When the film doped with Ms7 is exposed to a stream (250 mL·min−1) of gaseous mixture containing 200 ppb of $Cl_2$, the disappearance of the absorbance of Ms7 is observed, replaced by the appearance of a new absorption band centred around 267 nm. The reaction is very rapid and the species formed at 267 nm has a high molar extinction coefficient. From the measurements of the variation in absorbance at 192 nm or at 267 nm as a function of the $Cl_2$ content of the gaseous stream for a fixed flow rate, it is possible to plot calibration curves which serve to measure the $Cl_2$ content of a gaseous mixture of unknown composition, by exposing a film doped with Ms7 to this gaseous mixture.

The protocol used for the preparation of mesoporous thin films doped with Ms8 is identical to that presented for Ms5, the proportions and the values of the indicated parameters are similar. The film is heated with an infrared heating unit at a moderate temperature (160° C.) for 15 minutes in order to stiffen the inorganic network without destroying the probe molecules. During the exposure of the thin film to $Cl_2$, the molecules of pollutant diffuse rapidly via the porous network of the polymer towards Ms8. The detection of $Cl_2$ is optical. The absorbance of MS8 is measured in the UV. The latter reduces quantitatively with the addition of gaseous $Cl_2$ replaced by the appearance of two new bands centred at 295 and 370 nm (see FIG. 10).

The film of Ms9 is prepared from a solution of MS9 in water by spreading a drop of the solution over a quartz substrate. The solvent is evaporated by heating the film to 80° C. The reaction of Ms9 with $BCl_3$ was studied by exposing a film doped with Ms9 under reduced pressure to gaseous $BCl_3$ in a vacuum apparatus (see FIG. 8). MS9 reacts with $BCl_3$ like Ms1, $Ms_2$ and Ms8. The disappearance of the absorption band of Ms9 is observed centred at 220 nm and replaced by the appearance of two new bands centred at 295 and 370 nm. The same experiments were carried out at atmospheric pressure by exposing the film to a gaseous mixture containing a known $BF_3$ content. From the measurements of the variation in absorbance at 295 and 370 nm as a function of the $BCl_3$ content of the gaseous mixture and for a fixed flow rate, calibration curves are plotted. From these curves, the content of a gaseous mixture is determined, by exposing a film doped with Ms9 to this mixture.

Figure 12:
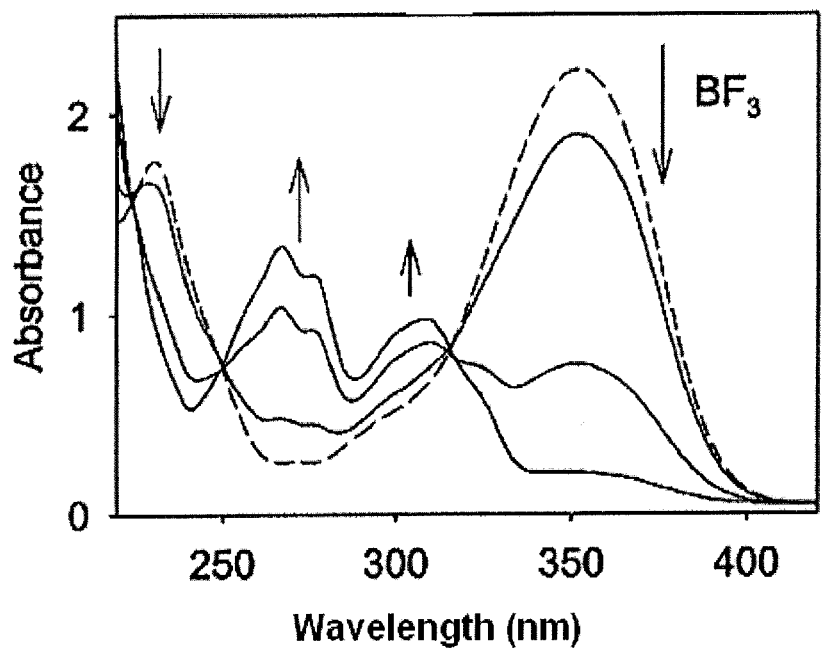
FIG. 12 represents the absorption spectrum of a coumarin in ethanol and its development during the addition of aliquots of $BF_3$.
Figure 13:
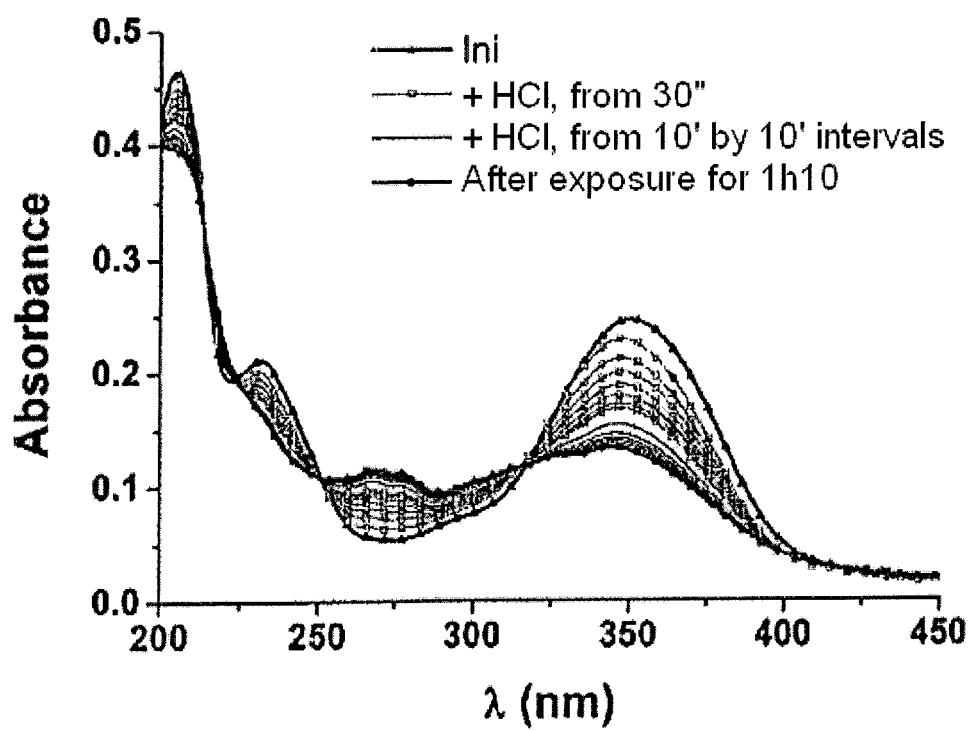
FIG. 13 represents the absorption spectrum of a coumarin in a porous matrix and its development during the exposure of the matrix to gaseous HCl (45 ppm).

The reactivity of the probe molecules of the family of the coumarins is shown in FIGS. 12 and 13 with the examples of coumarin 120, Ms10, in solution and incorporated in a porous matrix.

In the first example, a 5 $10^{-4}$ mol·L$^{-1}$ solution of coumarin 120 in methanol is prepared. Aliquots are taken from a 1.3 mol·L$^{-1}$ stock solution of $BF_3$ in methanol in order to prepare several 5 $10^{-4}$ mol·L$^{-1}$ solutions of coumarin containing $10^{-3}$, $10^{-2}$ and $10^{-1}$ mol·L$^{-1}$ of $BF_3$. The spectral variations observed in FIG. 12 show the disappearance of the absorption bands of the coumarin 120 to be replaced by a new species exhibiting two absorption bands between 230 and 330 nm, in a wavelength range where the coumarin absorbs little. It is possible to observe the same spectral variations during the addition of aliquots from an aqueous solution of hydrochloric acid (HCl). From the variation in absorbances at 350 nm or at 270 nm as a function of the concentration of $BF_3$, it is possible to plot calibration curves which serve for the detection and measuring of $BF_3$.

The coumarin 120 being fluorescent, advantage was also taken of the variations in intensity of fluorescence of the coumarin in the presence of $BX_3$ for measuring these pollutants. Other coumarins and more particularly C522, C500, C102 or also C47 were also used for the measurement of $BX_3$ or HX by absorption or fluorescence.

In the 2$^{nd}$ example, the coumarin is incorporated in a nanoporous matrix. For this purpose a solution of precursors is prepared containing tetra-methoxy silane (TMOS), ethanol, tetrahydroxyfuran, water and coumarin 120 in the molar proportions TMOS:EtOH:THF:$H_2O$:C120=1:1.95:1.4:4:0.0124. This mixture is stirred under ultrasound for 5 minutes then left to mature for 24 hours in a hermetic flask. Thin films of the mesoporous material are obtained by depositing a fine layer of the sol on a quartz slide by the dip-coating method with a constant withdrawal speed. The speed used is 3 mm. s$^{-1}$. During the deposition, the humidity level in the chamber of the device is fixed at a value comprised between 15 and 30%. During the exposure of the thin film to HCl, the coumarin reacts with HCl and the detection is carried out by an optical measurement. The coumarin being fluorescent, it is possible to monitor the variations in the absorbance spectra on film and the fluorescence at the same time. The initial absorption spectrum of the film comprises three bands having maximum values at 206, 234 and 348 nm (see FIG. 13). Before exposure, when the film is excited at 350 nm, it is fluorescent with maximum intensity at 440 nm. When the film doped with Ms10 is exposed to a stream (50 mL·min−1) of gaseous mixture containing 45 ppm of HCl, a reduction in the absorbance at 234 and 348 nm and the appearance of two absorbance bands at 265 and 278 nm are observed. Concomitantly, a reduction in the fluorescence emission of the film is observed. From the measurements of the variation in absorbance and/or fluorescence as a function of the HCl content of the gaseous stream for a fixed flow rate, it is possible to plot calibration curves which serve to measure the HCl content of a gaseous mixture of unknown composition.

Figure 14:
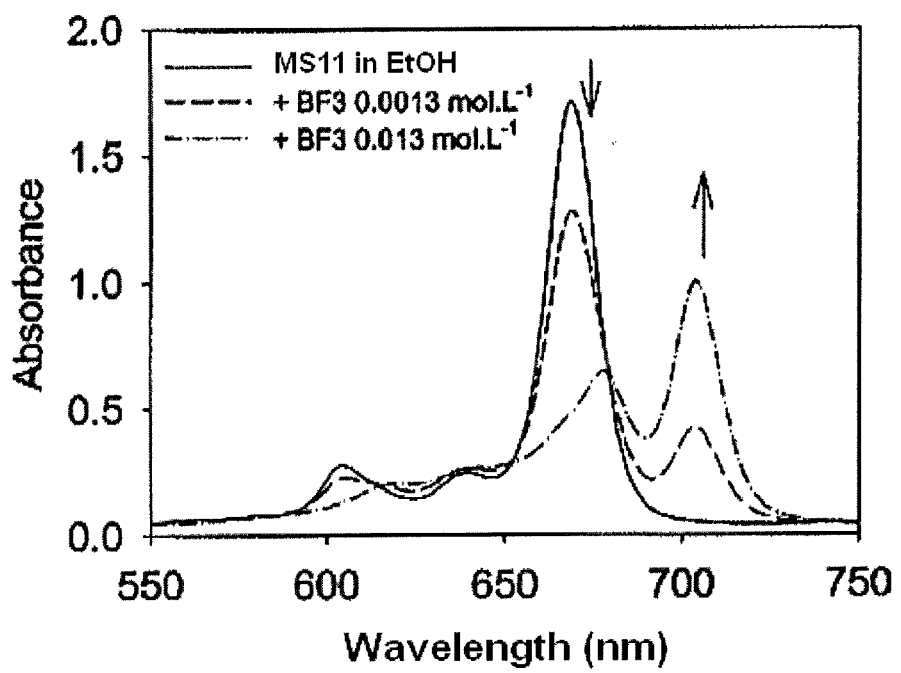
FIG. 14 represents the absorption spectrum of a magnesium phthalocyanine in ethanol and its development during the addition of aliquots of $BF_3$.
Figure 15:
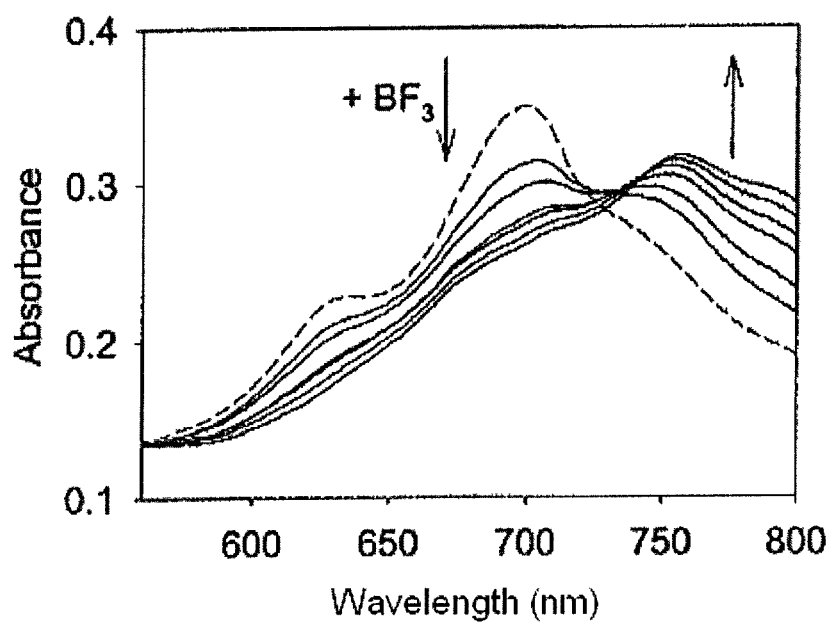
FIG. 15 represents the absorption spectrum of a magnesium phthalocyanine deposited on a glass slide by evaporation of the solvent and its development during the exposure of the film under reduced pressure to $BF_3$ (1 torr).
Figure 16:
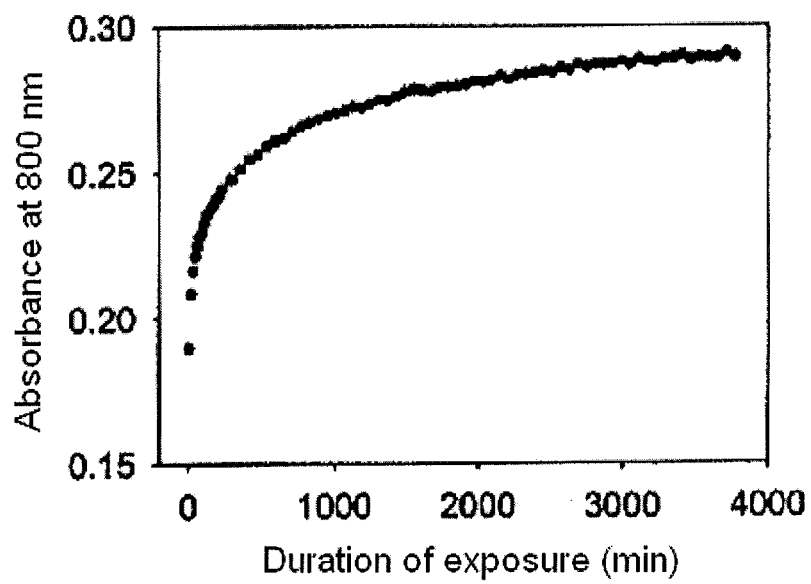
FIG. 16 represents the monitoring of the appearance kinetics of the product of the reaction between the magnesium phthalocyanine and $BF_3$ at 800 nm

Advantage is also taken of the reactivity of the tetrabenzoporphyrazins for the detection of $BX_3$ or HX in solution and in gaseous phase. A 1st example is shown with Ms11 used either in solution, or deposited on a glass slide (see FIGS. 14 to 16).

In the first case, a $10^{-5}$ mol·$L^{-1}$ solution of Ms11 in ethanol is prepared to which aliquots of a 1.3 mol·$L^{-1}$ stock solution of $BF_3$, in ethanol, are added. Various solutions of Ms11 containing $BF_3$ at different concentrations, 1.3 $10^{-3}$ and 1.3 $10^{-2}$ mol·$L^{-1}$, are thus obtained. In the presence of $BF_3$, the "Q" band, typical of the visible absorption spectrum of a tetrabenzoporphyrazin of D4h symmetry, reduces and disappears to be replaced by a new absorption band of different symmetry, corresponding to the species originating from the reaction of $BF_3$ with the nitrogen atoms of the aza bridges of the macrocycle (see FIG. 14). By measuring the variations in absorbance beyond 700 nm in the region where only the new species absorbs and as a function of the $BF_3$ concentration, calibration curves were plotted. Starting with the latter, $BF_3$ dissolved in a solution containing Ms11 was assayed. The tetrabenzoporphyrazins being fluorescent, the variations in intensity of fluorescence were also measured as a function of the $BF_3$ concentration.

Ms11 was also deposited by spreading a drop of solution of Ms11 in ethanol on glass. After drying, an absorption spectrum of Ms11 is obtained which is different from that obtained in solution and which corresponds to the aggregation of the molecules of Ms11 on the substrate. When the film of Ms11 is exposed to a reduced pressure of $BF_3$ in a vacuum apparatus, it is possible to observe, as in solution, a significant bathochromic shift in the absorption spectrum of Ms11 (see FIGS. 15 and 16). The variation in intensity of the new absorption band in a wavelength range where Ms11 does not absorb can be quantitatively correlated with the $BF_3$ concentration.

Figure 17:
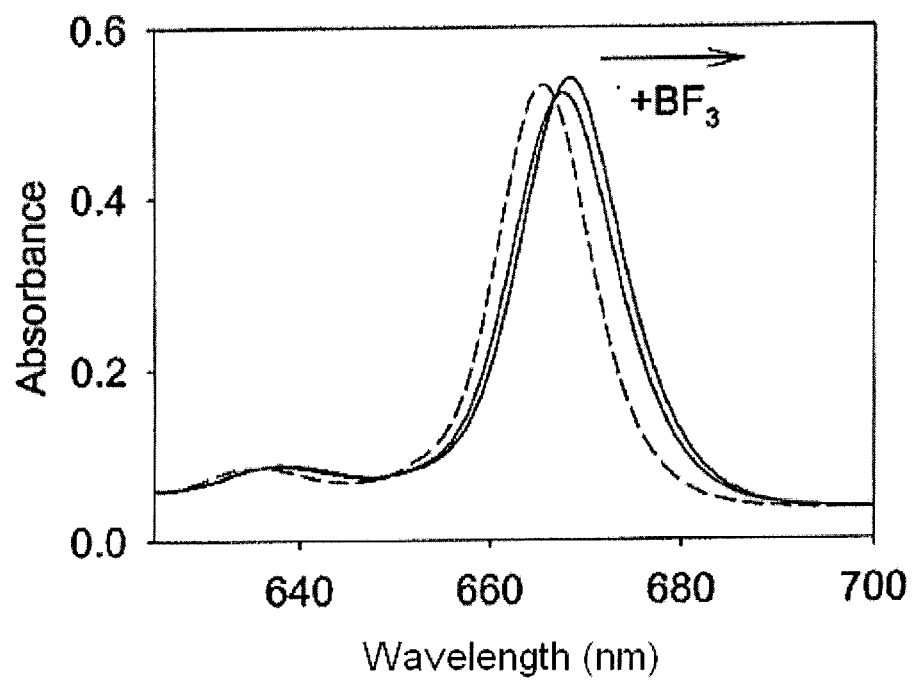
FIG. 17 represents the absorption spectrum of a silicon phthalocyanine in ethanol and its development during the addition of aliquots of $BF_3$ (1.3M)
Figure 18:
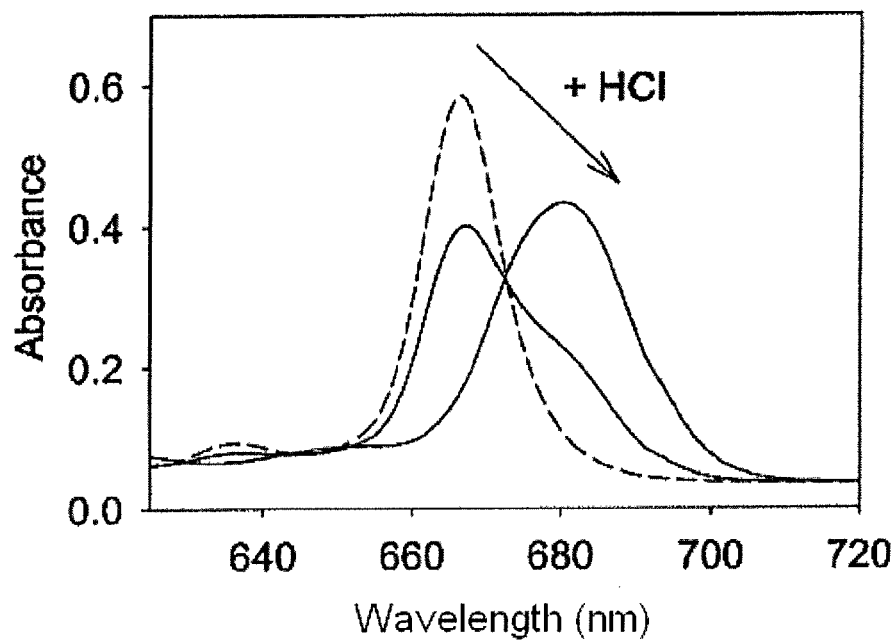
FIG. 18 represents the absorption spectrum of a silicon phthalocyanine in water and its development during the addition of HCl (1 and 12M).

A second example of a study of the reactivity of a tetrabenzoporphyrazin, Ms12, which differs from Ms11 by the nature of the central metal, is shown in FIG. 17. In solution, the reactivity of Ms12 vis-à-vis $BF_3$ and HCl is very different. A slight bathochromic shift is observed in the presence of $BF_3$ in large excess whereas the successive protonation of the nitrogen atoms of the aza bridges of the macrocycle is observed in the presence of HCl (see FIG. 18).

Figure 19:
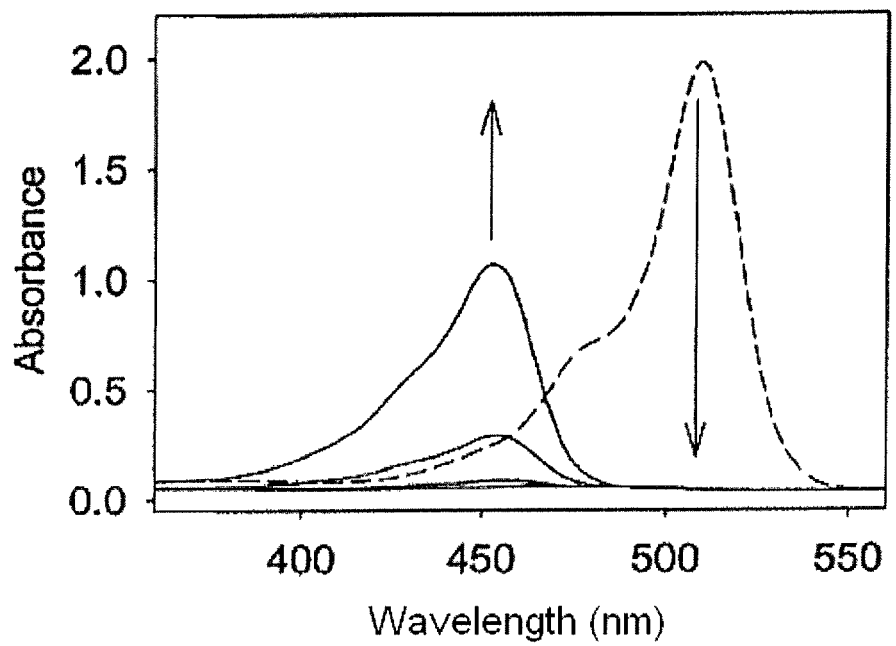
FIG. 19 represents the absorption spectrum of a fluorescein in methanol and its development during the addition of aliquots of $BF_3$.

The reactivity of the fluorescein (Ms14) with $BX_3$ and HCl in solution or in gaseous phase was studied. Ms14 reacts very effectively in solution with $BF_3$, $BCl_3$ and HCl. An example of the reaction of $10^{-4}$ mol·$L^{-1}$ Ms14 in methanol in the presence of $BF_3$ at various concentrations ($10^{-3}$, $10^{-2}$ and $10^{-1}$ mol·$L^{-1}$) is shown in FIG. 19. During the interaction of $BF_3$ with one of the two ternary nitrogen atoms the disappearance of the two UV absorption bands of Ms14 between 230 and 330 nm is observed. With larger additions of $BF_3$, the interaction of $BF_3$ with the last ternary nitrogen atom completely interrupts the delocalization of the electrons in the macrocycle. The absorption band of Ms14, which is very intense in the visible range between 425 and 550 nm, disappears to be replaced by a new band shifted towards the blue. It is possible to quantitatively correlate the variation in absorbance of Ms14 at 260 nm and at 510 nm as a function of the $BF_3$ concentration. Moreover, as Ms14 is highly fluorescent, the variations in the intensity of the fluorescence band of Ms14 were correlated as a function of the $BF_3$ concentration. The same reactions are observed with $BCl_3$ and HCl.

Figure 20:
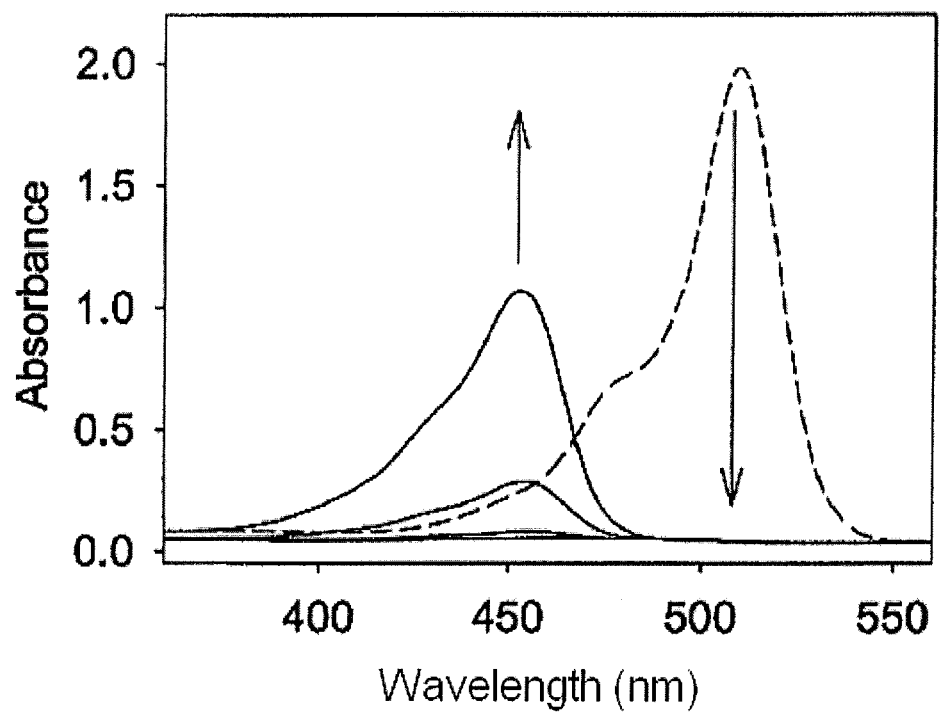
FIG. 20 represents the absorption spectrum of a composition containing fluorescein and CTAB deposited on a glass slide and its development during the exposure of the film under reduced pressure to gaseous $BCl_3$.

Ms14, solubilized with a surfactant (CTAB) in methanol was also deposited on a quartz slide then exposed to a reduced pressure of $BCl_3$ (0.48 torr) (FIG. 20). The reaction observed in solid phase is similar to that in solution. By measuring the variations in absorbance at 525 nm (or in fluorescence at 600 nm) of Ms14 as a function of the gaseous $BX_3$ content, it is possible to establish the calibration curves for the assay of $BX_3$ in a gaseous mixture.

Figure 21:
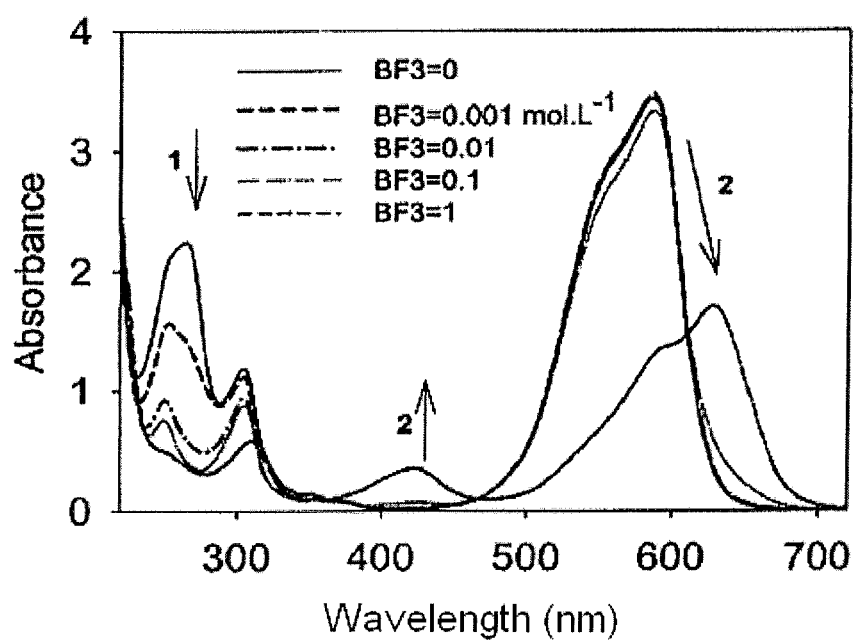
FIG. 21 represents the absorption spectrum of crystal violet in methanol and its development during the addition of aliquots of $BF_3$.

Crystal violet (Ms15) illustrates the use of the triarylmethanes and more particularly of the aminotriarylmethanes as probe molecules. Ms15 reacts with $BX_3$ and HCl both in solution and in the gaseous phase. FIG. 21 shows the spectral variations observed when aliquots of a 1.3 mol·$L^{-1}$ solution of $BF_3$ in methanol are added to a 5 $10^{-4}$ mol·$L^{-1}$ solution of Ms15. In a first step 1, even though virtually no spectral variation of Ms15 is observed in the visible range, the intensity of the UV bands between 200 and 330 nm decreases with the increase in the $BF_3$ concentration from $10^{-3}$ to $10^{-1}$ mol·$L^{-1}$. The increase in the intensity of the new bands in the UV range can be quantitatively correlated with the $BF_3$ concentration having reacted with one of the nitrogen sites of Ms15. In step 2, in the presence of a large excess of $BF_3$ (1 mol·$L^{-1}$), the absorption band of Ms15 in the visible (570 nm) as well as the UV bands between 230 and 330 nm disappear to be replaced by two new bands in the visible range, one of low intensity centred at 430 nm and the second of higher intensity the maximum absorption of which is situated at 630 nm. These new bands correspond to Ms15 all the nitrogen sites of which have reacted with $BF_3$. The variation in intensity of the band at 570 or at 650 nm can be quantitatively correlated with the concentration of molecules of $BF_3$. $BCl_3$ and HCl react in the same manner with Ms15.

Figure 22:
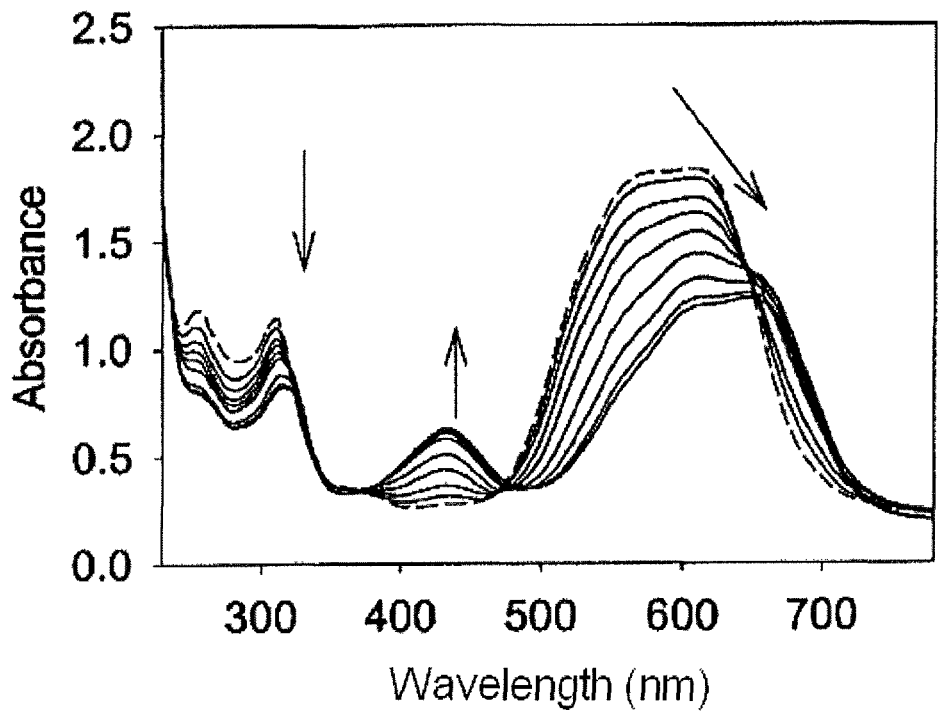
FIG. 22 represents the absorption spectrum of the crystal violet deposited on a quartz substrate by evaporation of the solvent and its development during the exposure of the film under reduced pressure to gaseous HCl (4 torr)

Ms15 can be deposited on a quartz substrate by spreading a drop of a 5 $10^{-4}$ mol·$L^{-1}$ solution of Ms15 in methanol on the substrate. After drying, the film of Ms15 exhibits a spectrum similar to that found in solution (FIG. 22). The film is exposed under reduced pressure (4 torr) to gaseous HCl in a vacuum apparatus. At this pressure, the number of HCl molecules is high and the reaction with the first nitrogenous site of Ms15 is immediate. The collection of the spectra 2 minutes after the exposure already shows the second reaction of HCl with the second nitrogenous site of Ms15. The same spectral variation is obtained as that observed in solution with the excess of $BF_3$, namely the disappearance of the band at 570 and bands in the UV range replaced by the appearance of two new bands at 430 and 660 nm (see FIG. 22).

The reaction is reversible. By pumping the film of Ms15 under vacuum, the initial spectrum of Ms15 is again found.

Finally, a mixture of two probe molecules, Ms13 and Ms15, present in the formulation of BIC® (the formulation contains 3 dyes: Yellow 47 (CAS: 71077-14-0), Violet 9 (CAS: 467-63-0) and Solvent blue 38 (CAS: 1330-38-7)) not forming a matrix was used either directly on a mica slide or in solution.

Figure 23:
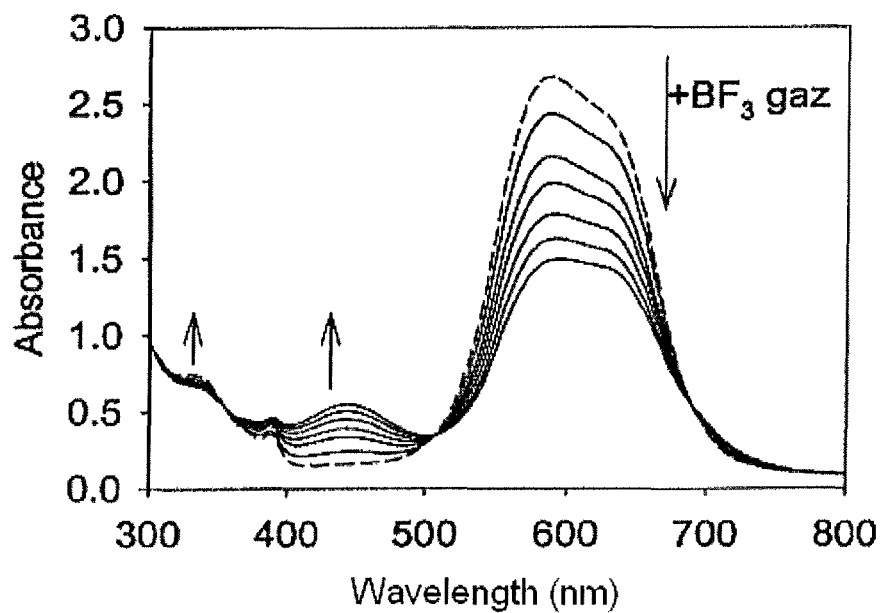
FIG. 23 represents the absorption spectrum of a composition of BIC® deposited on glass and its development during the exposure of the film under reduced pressure to $BF_3$ (2 torr).

A first experiment is carried out by depositing the mixture on a glass substrate. The sample was then exposed under reduced pressure to $BF_3$ in a vacuum apparatus. In the presence of $BF_3$ at 1 torr, it is noted that Ms15 is most reactive vis-à-vis the $BF_3$ as the spectral variations already correspond to step 2 of complexation of the $2^{nd}$ nitrogenous site of MS15, step 1 of complexation of a nitrogenous site by $BF_3$ being already finished (see FIG. 23).

Figure 24:
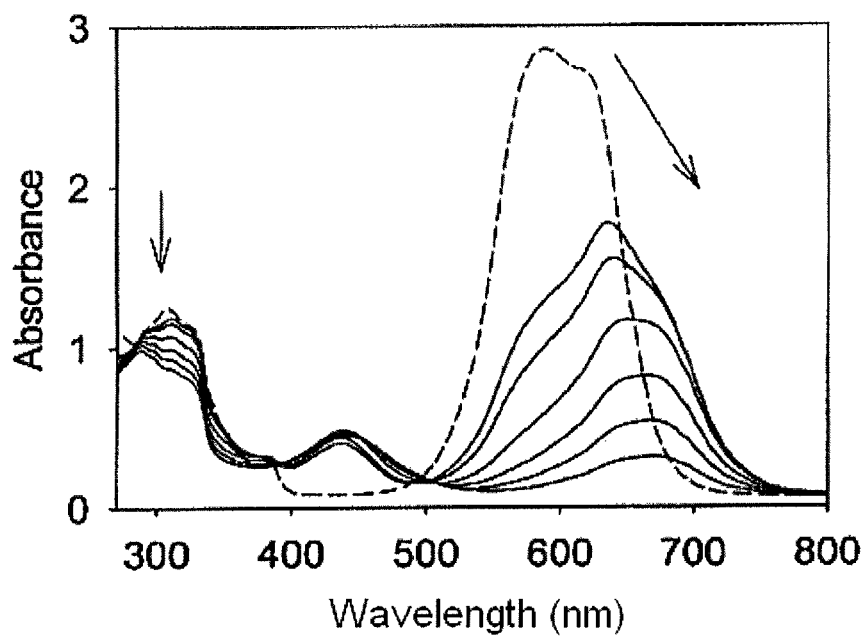
FIG. 24 represents the absorption spectrum of a composition of BIC® in ethanol and its development during the addition of aliquots of HCl.

A similar result is observed when the Ms13+Ms15 mixture is in solution in ethanol. The addition of HCl induces a rapid protonation of the nitrogenous sites of Ms15. The spectral variations correspond to the end of step 2, during which HCl also reacts with Ms13 (FIG. 24).

Therefore, it is possible to mix different probe molecules with each other.

3. Quantification of $X_2$-Type Compounds

It is also possible to quantify the content of halogen compounds of a gaseous stream by quantitatively measuring a physico-chemical property the variation of which is dependent on the content of gaseous halogen compounds.

For example, for a thin film doped with MS7, a new absorption band with a maximum at 267 nm is observed when it is exposed to a gaseous stream containing chlorine. The intensity of this band increases with exposure. The measurement of the speed of the variation in absorbance at 267 nm for different chlorine contents showed that this speed varies with the chlorine content and that it is therefore possible to establish a calibration curve for the sensor by representing the speed of variation in absorbance as a function of the chlorine content in the stream.

Figure 25:
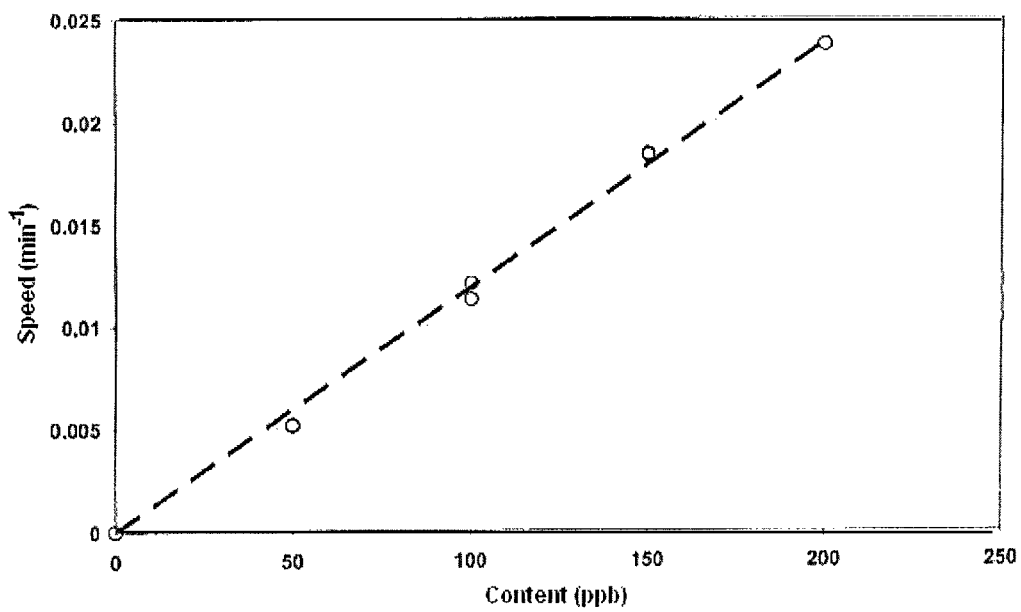
FIG. 25 is an example of a calibration curve obtained for a thin film doped with MS7 and deposited by dipping on each surface of a quartz slide.

FIG. 25 is an example of a calibration curve obtained for a thin film doped with MS7 and deposited by dipping on each surface of a quartz slide. This film was continuously exposed to a stream of nitrogen of 500 mL·min−1 in which the $Cl_2$ content varied between 40 and 200 ppb for short periods (<5 min). The sequence applied in this example is as follows: 0, 50; 50; 100; 100; 150; 150; 200 and 200 ppb.

Another example relates to a thin film doped with MS8. In this case, two new absorption bands with maximum values at 288 and 350 nm are observed when the film is exposed to a gaseous stream containing chlorine. The intensity of these bands increases with exposure. The measurement of the speed of the variation in absorbance at 292 nm for different chlorine contents showed that this speed varies with the chlorine content in the stream and as a function of the initial quantity of MS8 in the film. It is therefore possible to establish a calibration curve for the sensor by representing the speed of variation in absorbance standardized with respect to the MS8 content in the film as a function of the chlorine content in the stream.

Figure 26:
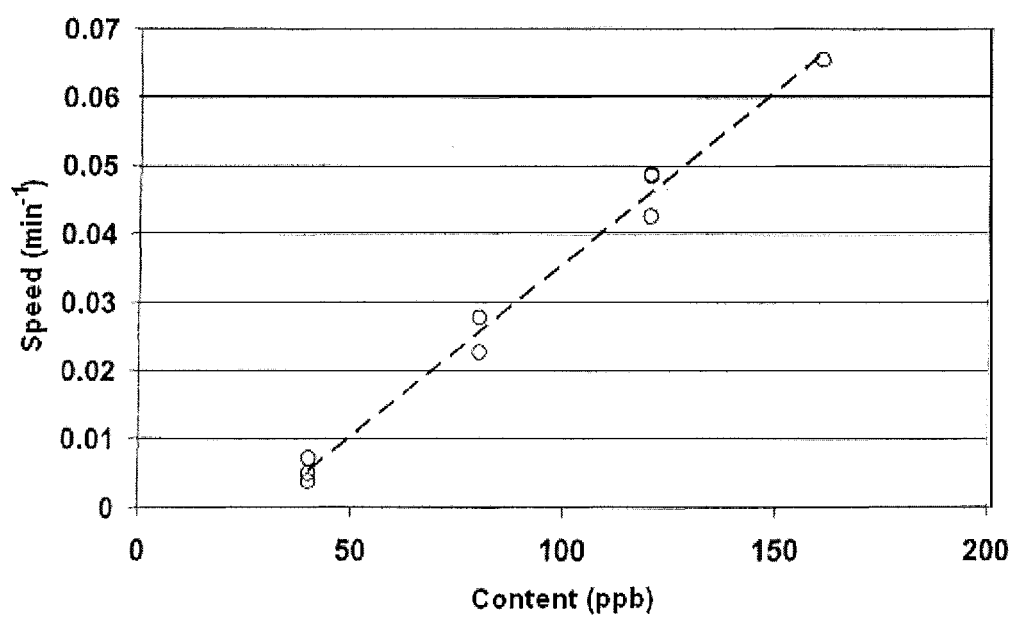
FIG. 26 is an example of a calibration curve obtained for a thin film doped with MS8 and deposited by dipping.

FIG. 26 is an example of a calibration curve obtained for a thin film doped with MS8 and deposited by dipping. This film was continuously exposed to a stream of nitrogen of 500 mL·min$^{-1}$ in which the $Cl_2$ content varied between 40 and 160 ppb for short periods (<5 min). The sequence applied in this example is as follows: 40; 40; 40; 80; 80; 120; 120 and 160 ppb.

4. Cells for Trapping Compounds of $BX_3$, HX or $X_2$ Type

Trapping cells were produced from a glass tube with a diameter of 1.6 cm and length of 1000 cm wound helically about a central axis. A total volume of 2 liters is thus available for treatment of the polluted air and a surface of 5024 cm$^2$ for the deposition of a film of porous material doped with probe molecules. The helical structure of the trapping cell makes it possible to slow down the diffusion of the gas and improve the contact between the pollutant molecules and the porous film and therefore the trapping of the pollutant.

From 500 cm$^3$ of a Sol-Gel solution of silica precursors containing 5 10$^{-4}$ mol·L$^{-1}$ probe molecules of Ms15, a thin film of porous material doped with Ms15 is deposited on the inner wall of the helical tube using a rotary evaporator. The tube being sealed by a stopper at one end, it is turned about its axis until the sol gels. After evaporation of the residual solvents, the deposited film has a thickness of approximately 124 µm and a violet colour.

The system was exposed to a stream containing the pollutant. When the violet colour has faded until it completely disappears, the trapping system has been saturated. Downstream of the tube, a suction pump is mounted.

5. Trapping of Compounds of $BX_3$, HX or $X_2$ Type

With the trapping cell described above, the total number of moles of Ms15 is 2.5 10$^{-4}$ mole. It is possible to pump air containing 100 ppb of $BF_3$ through this cell at a flow rate of 1 L·min$^{-1}$ for 930 hours. The volume of air treated is in this case 55.8 m$^3$.

The invention claimed is:

1. A process for detecting a gaseous compound of $BX_3$, HX or $X_2$ type within a gas using a composition containing a probe molecule, wherein the probe molecule is a molecule for which the reaction with one or more gaseous compounds of $BX_3$, HX or $X_2$ type leads to a variation of at least one of its spectral properties, this variation being measurable by a suitable analysis technique, wherein the probe molecule is selected from alkali metal halides, quaternary ammonium halides, coumarin and its derivatives, porphyrazine and its derivatives, fluorescein and its derivatives, triarylmethanes, rhodamines, cresyl violet, derivatives of phenoxazine and oxazones, wherein the probe molecule is incorporated in a porous sol-gel matrix, having pores of diameter less than 20 Angstroms, based on inorganic polymers or organic-inorganic hybrids and wherein the following steps are carried out in this order:
   (a) measurement of said spectral property of the probe molecule prior to reaction with said one or more gaseous compounds,
   (b) repeat measurement of said spectral property after reaction with said one or more gaseous compounds,
   (c) correlation of the variation of said spectral property between the step of prior measurement of said spectral property of the composition (step (a)) and step (b) in the presence of said gaseous compound of $BX_3$, HX or $X_2$ type.

2. A process according to claim 1, wherein, in step (c), the amount of change between the measurements of steps (a) and (b) is calculated, from which the amount of gaseous compound present is determined.

3. A process according to claim 1, wherein said spectral property is absorbance or fluorescence.

4. A process according to claim 1, wherein the probe molecule has a polymeric structure.

5. A process according to claim 1, wherein the gas is brought into contact with the composition comprising the probe molecule in the form of a gaseous stream.

6. A process for detecting a gaseous compound of $BX_3$, HX or $X_2$ type within a gas using a composition containing a probe molecule, wherein the probe molecule is a molecule for which the reaction with one or more gaseous compounds of $BX_3$, HX or $X_2$ type leads to a variation of at least one of its spectral properties, this variation being measurable by a suitable analysis technique, wherein said spectral property of said probe molecule has a known value prior to commencement of the process, wherein the probe molecule is selected from alkali metal halides, quaternary ammonium halides, coumarin and its derivatives, porphyrazine and its derivatives, fluorescein and its derivative, triarylmethanes, rhodamines, cresyl violet, derivatives of phenoxazine and oxazones, wherein the probe molecule is incorporated in a porous sol-gel matrix, having pores of diameter less than 20 Angstroms, based on inorganic polymers or organic-inorganic hybrids and wherein the following steps are carried out in this order:
   (a) providing a probe molecule having a spectral property of known value prior to reaction with said one or more gaseous compounds,
   (b) measurement of said spectral property after reaction with said one or more gaseous compounds, (c) correlation of the variation of said spectral property between the known value of step (a) and the measured value of step (b) in the presence of said gaseous compound of $BX_3$, $HX$ and $X_2$ type.

7. A process according to claim 6, wherein, in step (c), the amount of change between the spectral properties of steps (a) and (b) is calculated, from which the amount of gaseous compound present is determined.

8. A process according to claim 6, wherein said spectral property is absorbance or fluorescence.

9. A process according to claim 6, wherein the probe molecule has a polymeric structure.

10. A process according to claim 6, wherein the gas is brought into contact with the composition comprising the probe molecule in the form of a gaseous stream.

* * * * *